(12) United States Patent
Francischelli et al.

(10) Patent No.: US 7,824,399 B2
(45) Date of Patent: *Nov. 2, 2010

(54) ABLATION SYSTEM AND METHOD OF USE

(75) Inventors: David E. Francischelli, Anoka, MN (US); Eduardo N. Warman, Maple Grove, MN (US); Rahul Mehra, Stillwater, MN (US); Mark T. Stewart, Lino Lakes, MN (US); James R. Skarda, Lake Elmo, MN (US); Harry Puryear, Shoreview, MN (US); David Schwartzman, Pittsburgh, PA (US)

(73) Assignee: Medtronic, Inc., Minneapolis, MN (US)

( * ) Notice: Subject to any disclaimer, the term of this patent is extended or adjusted under 35 U.S.C. 154(b) by 1288 days.

This patent is subject to a terminal disclaimer.

(21) Appl. No.: 11/355,465

(22) Filed: Feb. 16, 2006

(65) Prior Publication Data

US 2006/0142753 A1    Jun. 29, 2006

Related U.S. Application Data

(63) Continuation of application No. 10/685,236, filed on Oct. 14, 2003, now Pat. No. 7,029,470, which is a continuation of application No. 10/132,392, filed on Apr. 24, 2002, now Pat. No. 6,663,627.

(51) Int. Cl.
*A61B 18/18* (2006.01)

(52) U.S. Cl. .................. 606/34; 606/41; 600/508; 607/122

(58) Field of Classification Search ........... 606/32–34, 606/41–42; 607/101, 102, 116, 122; 600/508, 600/510

See application file for complete search history.

(56) References Cited

U.S. PATENT DOCUMENTS

| | | | |
|---|---|---|---|
| 3,736,936 A | 6/1973 | Basiulis et al. |
| 3,807,403 A | 4/1974 | Stumpf et al. |
| 3,823,575 A | 7/1974 | Parel |
| 3,823,718 A | 7/1974 | Tromovitch |

(Continued)

FOREIGN PATENT DOCUMENTS

EP    0 499 491 A2    2/1992

OTHER PUBLICATIONS

Chitwood, "Will C. Sealy, MD: The Father of Arrhythmia Surgery—The Story of the Fisherman with a Fast Pulse," Annals of Thoracic Surgery 58:1228-1239, 1994.

(Continued)

*Primary Examiner*—Linda C Dvorak
*Assistant Examiner*—Samantha Muro
(74) *Attorney, Agent, or Firm*—Mike Jaro; Jeffrey J. Hohenshell

(57) ABSTRACT

A system and method for creating lesions and assessing their completeness or transmurality. Assessment of transmurality of a lesion is accomplished by monitoring the depolarization signal in a local electrogram taken using electrodes located adjacent the tissue to be ablated. Following onset of application of ablation energy to heart tissue, the local electrogram is measured with electrodes located adjacent tissue to be ablated so that the ablation energy to ablation elements can be selectively reduced or terminated when transmurality is detected.

33 Claims, 11 Drawing Sheets

U.S. PATENT DOCUMENTS

| | | | |
|---|---|---|---|
| 3,827,436 | A | 8/1974 | Stumpf et al. |
| 3,830,239 | A | 8/1974 | Stumpf |
| 3,859,986 | A | 1/1975 | Okada et al. |
| 3,862,627 | A | 1/1975 | Hans, Sr. |
| 3,886,945 | A | 6/1975 | Stumpf et al. |
| 3,907,339 | A | 9/1975 | Stumpf et al. |
| 3,910,277 | A | 10/1975 | Zimmer |
| 3,913,581 | A | 10/1975 | Ritson et al. |
| 3,924,628 | A | 12/1975 | Droegemueller et al. |
| 4,018,227 | A | 4/1977 | Wallach |
| 4,022,215 | A | 5/1977 | Benson |
| 4,061,135 | A | 12/1977 | Widran et al. |
| 4,063,560 | A | 12/1977 | Thomas et al. |
| 4,072,152 | A | 2/1978 | Linehan |
| 4,082,096 | A | 4/1978 | Benson |
| 4,207,897 | A | 6/1980 | Lloyd et al. |
| 4,248,224 | A | 2/1981 | Jones |
| 4,275,734 | A | 6/1981 | Mitchiner |
| 4,278,090 | A | 7/1981 | van Gerven |
| 4,377,168 | A | 3/1983 | Rzasa et al. |
| 4,519,389 | A | 5/1985 | Gudkin et al. |
| 4,598,698 | A | 7/1986 | Siegmund |
| 4,601,290 | A | 7/1986 | Effron et al. |
| 4,664,110 | A | 5/1987 | Schanzlin |
| 4,736,749 | A | 4/1988 | Lundback |
| 4,779,611 | A | 10/1988 | Grooters et al. |
| 4,802,475 | A | 2/1989 | Weshahy |
| 4,815,470 | A | 3/1989 | Curtis et al. |
| 4,872,346 | A | 10/1989 | Kelly-Fry et al. |
| 4,916,922 | A | 4/1990 | Mullens |
| 4,917,095 | A | 4/1990 | Fry et al. |
| 4,936,281 | A | 6/1990 | Stasz |
| 4,946,460 | A | 8/1990 | Merry et al. |
| 5,013,312 | A | 5/1991 | Parins et al. |
| 5,029,574 | A | 7/1991 | Shimamura et al. |
| 5,044,165 | A | 9/1991 | Linner et al. |
| 5,078,713 | A | 1/1992 | Varney |
| 5,080,102 | A | 1/1992 | Dory |
| 5,080,660 | A | 1/1992 | Buelina |
| 5,100,388 | A | 3/1992 | Behl et al. |
| 5,108,390 | A | 4/1992 | Potocky et al. |
| 5,147,355 | A | 9/1992 | Freidman et al. |
| 5,178,133 | A | 1/1993 | Pena |
| 5,207,674 | A | 5/1993 | Hamilton |
| 5,215,103 | A * | 6/1993 | Desai ..................... 606/46 |
| 5,217,860 | A | 6/1993 | Fahy et al. |
| 5,222,501 | A | 6/1993 | Ideker et al. |
| 5,224,943 | A | 7/1993 | Goddard |
| 5,228,923 | A | 7/1993 | Hed |
| 5,231,995 | A | 8/1993 | Desai |
| 5,232,516 | A | 8/1993 | Hed |
| 5,233,515 | A | 8/1993 | Cosman |
| 5,246,438 | A | 9/1993 | Langberg |
| 5,254,116 | A | 10/1993 | Baust et al. |
| 5,263,493 | A | 11/1993 | Avitall |
| 5,269,291 | A | 12/1993 | Carter |
| 5,275,595 | A | 1/1994 | Dobak, III |
| 5,277,201 | A | 1/1994 | Stern |
| 5,281,213 | A | 1/1994 | Milder et al. |
| 5,281,215 | A | 1/1994 | Milder |
| 5,295,484 | A | 3/1994 | Marcus et al. |
| 5,309,896 | A | 5/1994 | Moll et al. |
| 5,316,000 | A | 5/1994 | Chapelon et al. |
| 5,317,878 | A | 6/1994 | Bradshaw et al. |
| 5,318,525 | A | 6/1994 | West et al. |
| 5,322,520 | A | 6/1994 | Milder |
| 5,323,781 | A | 6/1994 | Ideker et al. |
| 5,324,255 | A | 6/1994 | Passafaro et al. |
| 5,324,284 | A | 6/1994 | Imran |
| 5,324,286 | A | 6/1994 | Fowler |
| 5,334,181 | A | 8/1994 | Rubinsky et al. |
| 5,334,193 | A | 8/1994 | Nardella |
| 5,348,554 | A | 9/1994 | Imran et al. |
| 5,353,783 | A | 10/1994 | Nakao et al. |
| 5,354,258 | A | 10/1994 | Dory |
| 5,361,752 | A | 11/1994 | Moll et al. |
| 5,385,148 | A | 1/1995 | Lesh et al. |
| 5,396,887 | A | 3/1995 | Imran |
| 5,397,304 | A | 3/1995 | Truckai |
| 5,400,770 | A | 3/1995 | Nakao et al. |
| 5,400,783 | A | 3/1995 | Pomeranz et al. |
| 5,403,309 | A | 4/1995 | Coleman et al. |
| 5,403,311 | A | 4/1995 | Abele et al. |
| 5,405,376 | A | 4/1995 | Mulier et al. |
| 5,409,483 | A | 4/1995 | Campbell et al. |
| 5,423,807 | A | 6/1995 | Milder |
| 5,423,811 | A | 6/1995 | Imran et al. |
| 5,427,119 | A | 6/1995 | Swartz et al. |
| 5,431,649 | A | 7/1995 | Mulier et al. |
| 5,433,708 | A | 7/1995 | Nichols et al. |
| 5,435,308 | A | 7/1995 | Gallup et al. |
| 5,437,651 | A | 8/1995 | Todd et al. |
| 5,443,463 | A | 8/1995 | Stern et al. |
| 5,443,470 | A | 8/1995 | Stern et al. |
| 5,450,843 | A | 9/1995 | Moll et al. |
| 5,450,846 | A | 9/1995 | Goldreyer |
| 5,452,582 | A | 9/1995 | Longsworth |
| 5,452,733 | A | 9/1995 | Sterman et al. |
| 5,462,545 | A | 10/1995 | Wang et al. |
| 5,465,717 | A | 11/1995 | Imran et al. |
| 5,469,853 | A | 11/1995 | Law et al. |
| 5,472,876 | A | 12/1995 | Fahy |
| 5,478,309 | A | 12/1995 | Sweezer et al. |
| 5,478,330 | A | 12/1995 | Imran et al. |
| 5,486,193 | A | 1/1996 | Bourne et al. |
| 5,487,385 | A | 1/1996 | Avitall |
| 5,487,757 | A | 1/1996 | Truckai et al. |
| 5,496,312 | A | 3/1996 | Klicek |
| 5,497,774 | A | 3/1996 | Swartz et al. |
| 5,498,248 | A | 3/1996 | Milder |
| 5,500,012 | A | 3/1996 | Brucker et al. |
| 5,505,730 | A | 4/1996 | Edwards |
| 5,516,505 | A | 5/1996 | McDow |
| 5,520,682 | A | 5/1996 | Baust et al. |
| 5,522,870 | A | 6/1996 | Ben-Zion |
| 5,536,267 | A | 7/1996 | Edwards et al. |
| 5,540,681 | A | 7/1996 | Strul et al. |
| 5,540,684 | A | 7/1996 | Hassler, Jr. |
| 5,545,195 | A | 8/1996 | Lennox et al. |
| 5,545,200 | A | 8/1996 | West et al. |
| 5,549,661 | A | 8/1996 | Kordis et al. |
| 5,555,883 | A | 9/1996 | Avitall |
| 5,558,671 | A | 9/1996 | Yates |
| 5,560,362 | A | 10/1996 | Sliwa, Jr. et al. |
| 5,562,720 | A | 10/1996 | Stern et al. |
| 5,562,721 | A | 10/1996 | Marchlinski et al. |
| 5,569,241 | A | 10/1996 | Edwards |
| 5,571,088 | A | 11/1996 | Lennox et al. |
| 5,571,215 | A | 11/1996 | Sterman et al. |
| 5,573,532 | A | 11/1996 | Chang et al. |
| 5,575,766 | A | 11/1996 | Swartz et al. |
| 5,575,788 | A | 11/1996 | Baker et al. |
| 5,575,810 | A | 11/1996 | Swanson et al. |
| 5,578,007 | A | 11/1996 | Imran |
| 5,579,764 | A | 12/1996 | Goldreyer |
| 5,582,609 | A | 12/1996 | Swanson et al. |
| 5,588,432 | A | 12/1996 | Crowley |
| 5,590,657 | A | 1/1997 | Cain et al. |
| 5,595,183 | A | 1/1997 | Swanson et al. |
| 5,607,462 | A | 3/1997 | Imran |
| 5,617,854 | A | 4/1997 | Munsif |
| 5,630,837 | A | 5/1997 | Crowley |
| 5,637,090 | A | 6/1997 | McGee et al. |
| 5,643,197 | A | 7/1997 | Brucker et al. |

| Patent | Date | Inventor |
|---|---|---|
| 5,656,029 A | 8/1997 | Imran et al. |
| 5,658,278 A | 8/1997 | Imran et al. |
| 5,671,747 A | 9/1997 | Connor |
| 5,673,695 A | 10/1997 | McGee et al. |
| 5,676,662 A | 10/1997 | Fleischhacker et al. |
| 5,676,692 A | 10/1997 | Sanghvi et al. |
| 5,676,693 A | 10/1997 | Lafontaine |
| 5,678,550 A | 10/1997 | Bassen et al. |
| 5,680,860 A | 10/1997 | Imran |
| 5,681,278 A | 10/1997 | Igo et al. |
| 5,681,308 A | 10/1997 | Edwards et al. |
| 5,687,723 A | 11/1997 | Avitall |
| 5,687,737 A | 11/1997 | Branham et al. |
| 5,688,267 A | 11/1997 | Panescu et al. |
| 5,690,611 A | 11/1997 | Swartz et al. |
| 5,697,536 A | 12/1997 | Eggers et al. |
| 5,697,882 A | 12/1997 | Eggers et al. |
| 5,697,925 A | 12/1997 | Taylor |
| 5,697,927 A | 12/1997 | Imran et al. |
| 5,697,928 A | 12/1997 | Walcott et al. |
| 5,713,942 A | 2/1998 | Stern et al. |
| 5,716,389 A | 2/1998 | Walinsky et al. |
| 5,718,241 A | 2/1998 | Ben-Haim et al. |
| 5,718,701 A | 2/1998 | Shai et al. |
| 5,720,775 A | 2/1998 | Larnard |
| 5,722,402 A | 3/1998 | Swanson et al. |
| 5,730,074 A | 3/1998 | Peter |
| 5,730,127 A | 3/1998 | Avitall |
| 5,730,704 A | 3/1998 | Avitall |
| 5,733,280 A | 3/1998 | Avitall |
| 5,735,280 A | 4/1998 | Sherman et al. |
| 5,735,290 A | 4/1998 | Sterman et al. |
| 5,755,760 A | 5/1998 | Maguire et al. |
| 5,769,846 A | 6/1998 | Edwards et al. |
| 5,782,828 A | 7/1998 | Chen et al. |
| 5,785,706 A | 7/1998 | Bednarek |
| 5,788,636 A | 8/1998 | Curley |
| 5,792,140 A | 8/1998 | Tu et al. |
| 5,797,960 A | 8/1998 | Stevens et al. |
| 5,800,428 A | 9/1998 | Nelson et al. |
| 5,800,482 A | 9/1998 | Pomeranz et al. |
| 5,810,802 A | 9/1998 | Panescu et al. |
| 5,827,216 A | 10/1998 | Igo et al. |
| 5,836,947 A | 11/1998 | Fleischman et al. |
| 5,840,030 A | 11/1998 | Ferek-Petric et al. |
| 5,844,349 A | 12/1998 | Oakley et al. |
| 5,846,187 A | 12/1998 | Wells et al. |
| 5,846,191 A | 12/1998 | Wells et al. |
| 5,849,028 A | 12/1998 | Chen |
| 5,871,523 A | 2/1999 | Fleischman et al. |
| 5,871,525 A | 2/1999 | Edwards et al. |
| 5,873,845 A | 2/1999 | Cline et al. |
| 5,876,399 A | 3/1999 | Chia et al. |
| 5,879,295 A | 3/1999 | Li et al. |
| 5,879,296 A | 3/1999 | Ockuly et al. |
| 5,881,732 A | 3/1999 | Sung et al. |
| 5,882,346 A | 3/1999 | Pomeranz et al. |
| 5,885,278 A | 3/1999 | Fleischman |
| 5,893,848 A | 4/1999 | Negus et al. |
| 5,895,417 A | 4/1999 | Pomeranz et al. |
| 5,897,533 A | 4/1999 | Glickman |
| 5,897,553 A | 4/1999 | Mulier |
| 5,897,554 A | 4/1999 | Chia et al. |
| 5,899,898 A | 5/1999 | Arless et al. |
| 5,899,899 A | 5/1999 | Arless et al. |
| 5,902,289 A | 5/1999 | Swartz et al. |
| 5,904,711 A | 5/1999 | Flom et al. |
| 5,906,580 A | 5/1999 | Kline-Schoder et al. |
| 5,906,587 A | 5/1999 | Zimmon |
| 5,906,606 A | 5/1999 | Chee et al. |
| 5,908,029 A | 6/1999 | Knudson et al. |
| 5,916,213 A | 6/1999 | Haissaguerre et al. |
| 5,916,214 A | 6/1999 | Cosio et al. |
| 5,921,924 A | 7/1999 | Avitall |
| 5,921,982 A | 7/1999 | Lesh et al. |
| 5,927,284 A | 7/1999 | Borst et al. |
| 5,928,191 A | 7/1999 | Houser et al. |
| 5,931,810 A | 8/1999 | Grabek |
| 5,931,848 A | 8/1999 | Saadat |
| 5,954,661 A | 9/1999 | Greenspon et al. |
| 5,957,961 A | 9/1999 | Maguire et al. |
| 5,971,980 A | 10/1999 | Sherman |
| 5,971,983 A | 10/1999 | Lesh |
| 5,993,447 A | 11/1999 | Blewett et al. |
| 6,007,499 A | 12/1999 | Martin et al. |
| 6,012,457 A | 1/2000 | Lesh |
| 6,016,811 A | 1/2000 | Knopp et al. |
| 6,042,556 A | 3/2000 | Beach et al. |
| 6,063,081 A | 5/2000 | Mulier |
| 6,066,136 A | 5/2000 | Geistert |
| 6,071,279 A | 6/2000 | Whayne et al. |
| 6,088,894 A | 7/2000 | Oakley |
| 6,096,037 A | 8/2000 | Mulier |
| 6,113,592 A | 9/2000 | Taylor |
| 6,117,101 A | 9/2000 | Diederich et al. |
| 6,120,496 A | 9/2000 | Whayne et al. |
| 6,142,993 A | 11/2000 | Whayne et al. |
| 6,142,994 A | 11/2000 | Swanson et al. |
| 6,152,920 A | 11/2000 | Thompson et al. |
| 6,161,543 A | 12/2000 | Cox et al. |
| 6,165,174 A | 12/2000 | Jacobs et al. |
| 6,183,468 B1 * | 2/2001 | Swanson et al. ............... 606/40 |
| 6,217,528 B1 | 4/2001 | Koblish et al. |
| 6,217,576 B1 | 4/2001 | Tu et al. |
| 6,224,592 B1 | 5/2001 | Eggers et al. |
| 6,231,518 B1 | 5/2001 | Grabek et al. |
| 6,235,024 B1 | 5/2001 | Tu |
| 6,236,883 B1 | 5/2001 | Ciaccio et al. |
| 6,237,605 B1 | 5/2001 | Vaska et al. |
| 6,238,347 B1 | 5/2001 | Nix et al. |
| 6,238,393 B1 | 5/2001 | Mulier |
| 6,245,061 B1 | 6/2001 | Panescu et al. |
| 6,245,064 B1 | 6/2001 | Lesh et al. |
| 6,245,065 B1 | 6/2001 | Panescu et al. |
| 6,251,092 B1 | 6/2001 | Qin et al. |
| 6,251,128 B1 | 6/2001 | Knopp et al. |
| 6,270,471 B1 | 8/2001 | Hechel et al. |
| 6,293,943 B1 | 9/2001 | Panescu et al. |
| 6,296,619 B1 | 10/2001 | Brisken et al. |
| 6,302,880 B1 | 10/2001 | Schaer |
| 6,311,692 B1 | 11/2001 | Vaska et al. |
| 6,312,383 B1 | 11/2001 | Lizzi et al. |
| 6,314,962 B1 | 11/2001 | Vaska et al. |
| 6,314,963 B1 | 11/2001 | Vaska et al. |
| 6,319,249 B1 | 11/2001 | Tollner |
| 6,325,797 B1 | 12/2001 | Stewart et al. |
| 6,328,736 B1 | 12/2001 | Mulier |
| 6,332,881 B1 | 12/2001 | Carner et al. |
| 6,358,248 B1 | 3/2002 | Mulier |
| 6,361,531 B1 | 3/2002 | Hissong |
| 6,364,876 B1 | 4/2002 | Erb et al. |
| 6,368,275 B1 | 4/2002 | Sliwa et al. |
| 6,371,955 B1 | 4/2002 | Fuimaono et al. |
| 6,383,151 B1 | 5/2002 | Diederich et al. |
| 6,385,472 B1 | 5/2002 | Hall et al. |
| 6,398,792 B1 | 6/2002 | O'Connor |
| 6,409,722 B1 | 6/2002 | Hoey et al. |
| 6,413,254 B1 | 7/2002 | Hissong et al. |
| 6,419,648 B1 | 7/2002 | Vitek et al. |
| 6,425,867 B1 | 7/2002 | Vaezy et al. |
| 6,430,426 B2 | 8/2002 | Avitall |
| 6,440,130 B1 | 8/2002 | Mulier |
| 6,443,952 B1 | 9/2002 | Mulier |
| 6,447,507 B1 | 9/2002 | Bednarek et al. |
| 6,461,314 B1 | 10/2002 | Pant et al. |
| 6,461,356 B1 | 10/2002 | Patterson |

| | | |
|---|---|---|
| 6,464,700 B1 | 10/2002 | Koblish et al. |
| 6,471,697 B1 | 10/2002 | Lesh |
| 6,471,698 B1 | 10/2002 | Edwards et al. |
| 6,474,340 B1 | 11/2002 | Vaska et al. |
| 6,475,216 B2 | 11/2002 | Mulier |
| 6,477,396 B1 | 11/2002 | Mest et al. |
| 6,484,727 B1 | 11/2002 | Vaska et al. |
| 6,488,680 B1 | 12/2002 | Francischelli |
| 6,502,575 B1 | 1/2003 | Jacobs et al. |
| 6,514,250 B1 | 2/2003 | Jahns |
| 6,522,905 B2 | 2/2003 | Desai |
| 6,522,930 B1 | 2/2003 | Schaer et al. |
| 6,527,767 B2 | 3/2003 | Wang et al. |
| 6,537,248 B2 | 3/2003 | Mulier |
| 6,537,272 B2 | 3/2003 | Christopherson et al. |
| 6,558,382 B2 | 5/2003 | Jahns |
| 6,584,345 B2 | 6/2003 | Govari |
| 6,584,360 B2 | 6/2003 | Francischelli |
| 6,585,732 B2 | 7/2003 | Mulier |
| 6,605,084 B2 | 8/2003 | Acker et al. |
| 6,610,055 B1 | 8/2003 | Swanson et al. |
| 6,610,060 B2 | 8/2003 | Mulier |
| 6,613,048 B2 | 9/2003 | Mulier |
| 6,645,199 B1 | 11/2003 | Jenkins et al. |
| 6,645,202 B1 | 11/2003 | Pless et al. |
| 6,648,883 B2 | 11/2003 | Francischelli |
| 6,656,175 B2 | 12/2003 | Francischelli |
| 6,663,627 B2 * | 12/2003 | Francischelli et al. ......... 606/41 |
| 6,692,450 B1 | 2/2004 | Coleman |
| 6,699,240 B2 | 3/2004 | Francischelli |
| 6,702,811 B2 | 3/2004 | Stewart et al. |
| 6,706,038 B2 | 3/2004 | Francischelli |
| 6,706,039 B2 | 3/2004 | Mulier |
| 6,716,211 B2 | 4/2004 | Mulier |
| 6,736,810 B2 | 5/2004 | Hoey |
| 6,755,827 B2 | 6/2004 | Mulier |
| 6,764,487 B2 | 7/2004 | Mulier |
| 6,773,433 B2 | 8/2004 | Stewart et al. |
| 6,776,780 B2 | 8/2004 | Mulier |
| 6,807,968 B2 | 10/2004 | Francischelli |
| 6,827,715 B2 | 12/2004 | Francischelli |
| 6,849,073 B2 | 2/2005 | Hoey |
| 6,858,028 B2 | 2/2005 | Mulier |
| 6,887,238 B2 | 5/2005 | Jahns |
| 6,899,711 B2 | 5/2005 | Stewart et al. |
| 6,911,019 B2 | 6/2005 | Mulier |
| 6,916,318 B2 | 7/2005 | Francischelli |
| 6,936,046 B2 | 8/2005 | Hissong |
| 6,949,097 B2 | 9/2005 | Stewart et al. |
| 6,949,098 B2 | 9/2005 | Mulier |
| 6,960,205 B2 | 11/2005 | Jahns |
| 6,962,589 B2 | 11/2005 | Mulier |
| 7,029,470 B2 * | 4/2006 | Francischelli et al. ......... 606/34 |
| 2003/0045872 A1 | 3/2003 | Jacobs |
| 2003/0144656 A1 | 7/2003 | Ocel |
| 2003/0191462 A1 | 10/2003 | Jacobs |
| 2003/0216724 A1 | 11/2003 | Jahns |
| 2004/0015106 A1 | 1/2004 | Coleman |
| 2004/0015219 A1 | 1/2004 | Francischelli |
| 2004/0044340 A1 | 3/2004 | Francischelli |
| 2004/0049179 A1 | 3/2004 | Francischelli |
| 2004/0078069 A1 | 4/2004 | Francischelli |
| 2004/0082948 A1 | 4/2004 | Stewart et al. |
| 2004/0087940 A1 | 5/2004 | Jahns |
| 2004/0092926 A1 | 5/2004 | Hoey |
| 2004/0138621 A1 | 7/2004 | Jahns |
| 2004/0138656 A1 | 7/2004 | Francischelli |
| 2004/0143260 A1 | 7/2004 | Francischelli |
| 2004/0186465 A1 | 9/2004 | Francischelli |
| 2004/0215183 A1 | 10/2004 | Hoey |
| 2004/0220560 A1 | 11/2004 | Briscoe |
| 2004/0236322 A1 | 11/2004 | Mulier |
| 2004/0267326 A1 | 12/2004 | Ocel |
| 2005/0010095 A1 | 1/2005 | Stewart et al. |
| 2005/0033280 A1 | 2/2005 | Francischelli |
| 2005/0090815 A1 | 4/2005 | Francischelli |
| 2005/0143729 A1 | 6/2005 | Francischelli |
| 2005/0165392 A1 | 7/2005 | Francischelli |
| 2005/0209564 A1 | 9/2005 | Bonner |
| 2005/0267454 A1 | 12/2005 | Hissong |
| 2006/0009756 A1 | 1/2006 | Francischelli |
| 2006/0009759 A1 | 1/2006 | Christian |

OTHER PUBLICATIONS

Gallagher et al., "Cryosurgical Ablation of Accessory Atrioventrical Connections: A Method for Correction of the Pre-excitation Syndrome," Circulation 55(3): 471-479, 1977.
Sealy, "Direct Surgical Treatment of Arrhythmias: The Last Frontier in Surgical Cardiology," Chest 75(5): T36-537, 1979.
Sealy, "The Evolution of the Surgical Methods for Interruption of Right Free Wall Kent Bundles," The Annals of Thoracic Surgery 36(1): 29-36, 1983.
Guiraudon et al., "Surgical Repair of Wolff-Parkinson-White Syndrome: A New Closed-Heart Techique," The Annals of Thoracic Surgery 37(1): 67-71, 1984.
Klein et al., "Surgical Correction of the Wolff-Parkinson-White Syndrome in the Closed Heart Using Cryosurgery: A Simplified Approach," JACC 3(2): 405-409, 1984.
Randall et al., "Local Epicardial Chemical Ablation of Vagal Input to Sino-Atrial and Atrioventricular Regions of the Canine Heart," Journal of the Autonomic Nervous System 11:145-159, 1984.
Guiraudon et al., "Surgical Ablation of Posterior Septal Accessory Pathways in the Wolf-Parkinson-White Syndrome by a Closed Heart Technique," Journal Thoracic Cardiovascular Surgery 92:406-413, 1986.
Gallagher et al., "Surgical Treatment of Arrhythmias," The American Journal of Cardiology 61:27A-44A, 1988.
Mahomed et al., "Surgical Division of Wolff-Parkinson-White Pathways Utilizing the Closed-Heart Technique: A 2-Year Experience in 47 Patients," The Annals of Thoracic Surgery 45(5): 495-504, 1988.
Cox et al., Surgery for Atrial Fibrillation; Seminars in Thoracic and Cardiovascular Surgery, vol. 1, No. 1 (Jul. 1989) pp. 67-73.
Bredikis and Bredikis; Surgery of Tachyarrhythmia: Intracardiac Closed Heart Cryoablation; PACE, vol. 13, pp. 1980-1984.
McCarthy et al., "Combined Treatment of Mitral Regurgitation and Atrial Fibrillation with Valvuloplasty and the Maze Procedure," The American Journal of Cardiology 71: 483-486, 1993.
Yamauchi et al. "Use of Intraoperative Mapping to Optimize Surgical Ablation of Atrial Flutter," The Annals of Thoracic Surgery 56: 337-342, 1993.
Graffigna et al., "Surgical Treatment of Wolff-Parkinson-White Syndrome: Epicardial Approach Without the Use of Cardiopulmonary Bypass," Journal of Cardiac Surgery 8: 108-116, 1993.
Siefert et al., "Radiofrequency Maze Ablation for Atrial Fibrillation," Circulation 90(4): I-594.
Surgical treatment of atrial fibrillation: a review; Europace (2004) 5, S20-S29.
Elvan et al., "Radiofrequency Catheter Ablation of the Atria Reduces Inducibility and Duration of Atrial Fibrillation in Dog," Circulation 91: 2235-2244, 1995.
Cox et al., "Modification of the Maze Procedure for Atrial Flutter and Atrial Fibrillation. I. Rational and Surgical Results," The Journal of Thoracic Cardiovascular Surgery 110: 473-484, 1995.
Cox, "The Maze III Procedure for Treatment of Atrial Fibrillation," Sabiston DC, ed Atlas of Cardiothoracic Surgery, Philadelphia: WB Saunders: 460-475, 1994.
Sueda et al., "Simple Left Atrial Procedure for Chronic Atrial Fibrillation Associated with Mitral Valve Disease," The Annals of Thoracic Surgery 62(6): 1796-1800, 1996.
Tsui et al., "Maze 3 for Atrial Fibrillation: Two Cuts Too Few?" PACE 17: 2163-2166, 1994.
Kosakai et al., "Cox Maze Procedure for Chronic Atrial Fibrillation Associated with Mitral Valve Disease," The Journal of Thoracic Cardiovascular Surgery 108: 1049-1055, 1994.

Cox et al., "The Surgical Treatment of Atrial Fibrillation, IV Surgical Technique," *J of Thorac Cardiovasc Surg*, 1991: 101: 584-593.

Nardella, "Radio Frequency Energy and Impedance Feedback," SPIE vol. 1068, Catheter Based Sensing and Imaging Technology (1989).

Avitall et. al., "A Thoracoscopic Approach to Ablate Atrial Fibrillation Via Linear Radiofrequency Lesion Generation on the Epicardium of Both Atria," PACE, Apr. 1996;19(Part II):626,#241.

Sie et al., "Radiofrequency Ablation of Atrial Fibrillation in Patients Undergoing Mitral Valve Surgery. First Experience," Circulation (Nov. 1996) 96:450,I-675,#3946.

Sie et al., "Radiofrequency Ablation of Atrial Fibrillation in Patients Undergoing Valve Surgery," Circulation (Nov. 1997) 84:I450,#2519.

Jais et al., "Catheter Ablation for Paroxysmal Atrial Fibrillation: High Success Rates with Ablation in the Left Atrium," Circulation (Nov. 1996) 94:I-675,#3946.

Cox, "Evolving Applications of the Maze Procedure for Atrial Fibrillation," Ann Thorac Surg, 1993;55:578-580.

Cox et al. "Five-Year Experience with the Maze Procedure for Atrial Fibrillation," Ann Thorac Surg, 1993; 56:814-824.

Avitall et al., "New Monitoring Criteria for Transmural Ablation of Atrial Tissues," Circulation, 1996;94(Supp 1):I-493, #2889.

Cox et al., "An 8 1/2 Year Clinical Experience with Surgery for Atrial Fibrillation," Annals of Surgery, 1996;224(3):267-275.

Haissaguerre et al., "Radiofrequency Catheter Ablation for Paroxysmal Atrial Fibrillation in Humans: Elaboration of a procedure based on electrophysiological data," Nonpharmacological Management of Atrial Fibrillation, 1997 pp. 257-279.

Haissaguerre et al., "Right and Left Atrial Radiofrequency Catheter Therapy of Paroxysmal Atrial Fibrillation," Journal of Cardiovascular Electrophysiology, 1996;7(12):1132-1144.

Haissaguerre et al., "Role of Catheter Ablation for Atrial Fibrillation," Current Opinion in Cardiology, 1997;12:18-23.

Kawaguchi et al., "Risks and Benefits of Combined Maze Procedure for Atrial Fibrillation Associated with Organic Heart Disease," JACC, 1996;28(4):985-990.

Cox, et al., "Perinodal cryosurgery for atrioventricular node reentry tachycardia in 23 patients," Journal of Thoracic and Cardiovascular Surgery, 99:3, Mar. 1990, pp. 440-450.

Cox, "Anatomic-Electrophysiologic Basis for the Surgical Treatment of Refractory Ischemic Ventricular Tachycardia," Annals of Surgery, Aug. 1983; 198:2;119-129.

Williams, et al., "Left atrial isolation," J Thorac Cardiovasc Surg; 1980; 80: 373-380.

Scheinman, "Catheter-based Techniques for Cure of Cardiac Arrhythmias," Advances in Cardiovascular Medicine, 1996, ISSN 1075-5527, pp. 93-100.

Sueda et al., "Efficacy of a Simple Left Atrial Procedure for Chronic Atrial Fibrillation in Mitral Valve Operations," Ann Thorac Surg, 1997;63:1070-1075.

Office Action dated May 17, 2005 from U.S. Appl. No. 10/685,236 (5 pages).

Reasons for allowance from the Notice of Allowance from U.S. Appl. No. 10/132,392 (7 pages).

* cited by examiner

ABLATION SYSTEM AND METHOD OF USE

RELATED US APPLICATION DATA

This application is a continuation of U.S. Ser. No. 10/685,236, filed. Oct. 14, 2003 by Francischelli et al., now U.S. Pat. No. 7,029,470, which is a continuation of U.S. Ser. No. 10/132,392, filed Apr. 24, 2002 by Francischelli et al., now U.S. Pat. No. 6,663,627, and also claims the benefit of Provisional U.S. Patent Application No. 60/236,923, filed Apr. 26, 2001 by Francischelli et al., incorporated herein by reference in its entirety.

BACKGROUND OF THE INVENTION

The present invention relates to tissue ablation devices generally and relates more particularly to devices adapted to ablate lines of tissue, for example for use in conjunction with an electrosurgical version of the Maze procedure.

The Maze procedure is a surgical intervention for patients with chronic atrial fibrillation (AF) that is resistant to other medical treatments. The operation employs incisions in the right and left atria which divide the atria into electrically isolated portions which in turn results in an orderly passage of the depolarization wave front from the sino-atrial node (SA Node) to the atrial-ventricular node (AV Node) while preventing reentrant wave front propagation. Although successful in treating AF, the surgical Maze procedure is quite complex and is currently performed by a limited number of highly skilled cardiac surgeons in conjunction with other open-heart procedures. As a result of the complexities of the surgical procedure, there has been an increased level of interest in procedures employing electrosurgical devices or other types of ablation devices, e.g. thermal ablation, micro-wave ablation, cryo-ablation or the like to ablate tissue along pathways approximating the incisions of the Maze procedure. Electrosurgical systems for performing such procedures are described in U.S. Pat. No. 5,916,213, issued to Hiassaguerre, et al. U.S. Pat. No. 5,957,961, issued to Maguire, et al. and U.S. Pat. No. 5,690,661, all incorporated herein by reference in their entireties. Cryo-ablation systems for performing such procedures are described in U.S. Pat. No. 5,733,280 issued to Avitall, also incorporated herein by reference in its entirety.

In conjunction with the use of electrosurgical ablation devices, various control mechanisms have been developed to control delivery of ablation energy to achieve the desired result of ablation, i.e. killing of cells at the ablation site while leaving the basic structure of the organ to be ablated intact. Such control systems include measurement of temperature and impedance at or adjacent to the ablation site, as are disclosed in U.S. Pat. No. 5,540,681, issued to Struhl, et al., incorporated herein by reference in its entirety.

Additionally, there has been substantial work done toward assuring that the ablation procedure is complete, i.e. that the ablation extends through the thickness of the tissue to be ablated, before terminating application of ablation energy. This desired result is some times referred to as a "transmural" ablation. For example, detection of a desired drop in electrical impedance at the electrode site as an indicator of transmurality is disclosed in U.S. Pat. No. 5,562,721 issued to Marchlinski et al, incorporated herein by reference in its entirety. Alternatively, detection of an impedance rise or an impedance rise following an impedance fall are disclosed in U.S. Pat. No. 5,558,671 issued to Yates and U.S. Pat. No. 5,540,684 issued to Hassler, respectively, also incorporated herein by reference in their entireties. Because ablated heart tissue is necrotic, it does not depolarize and therefore does not contribute to the depolarization signal. This fact has recently led some physicians to use the amplitude of a locally acquired electrogram signal to determine whether a lesion is complete. For example, during provision of R-F energy at a constant power level, the physician may monitor the amplitude of electrograms obtained using electrodes adjacent the ablation site, and, in response to a defined drop, e.g. 75%, may terminate provision of RF energy.

Three basic approaches have been employed to create elongated lesions using electrosurgical devices. The first approach is simply to create a series of short lesions using a contact electrode, moving it along the surface of the organ wall to be ablated to create a linear lesion. This can be accomplished either by making a series of lesions, moving the electrode between lesions or by dragging the electrode along the surface of the organ to be ablated and continuously applying ablation energy, as described in U.S. Pat. No. 5,897,533 issued to Mulier, et al., incorporated herein by reference in its entirety. The second basic approach to creation of elongated lesions is simply to employ an elongated electrode, and to place the elongated electrode along the desired line of lesion along the tissue. This approach is described in U.S. Pat. No. 5,916,213, cited above and. The third basic approach to creation of elongated lesions is to provide a series of electrodes and arrange the series of electrodes along the desired line of lesion. The electrodes may be activated individually or in sequence, as disclosed in U.S. Pat. No. 5,957,961, also cited above. In the case of multi-electrode devices, individual feedback regulation of ablated energy applied via the electrodes may also be employed. The present invention is believed useful in conjunction with all three approaches

SUMMARY OF THE INVENTION

The present invention is directed toward an improved system for creating lesions and assessing their completeness or transmurality. In the preferred embodiment as disclosed, the apparatus for producing the lesions is an electrosurgical device, in particular a saline-irrigated bipolar electrosurgical forceps. However, the mechanism for assessing lesion transmurality provided by the present invention is believed useful in other contexts, including unipolar R-F ablation and R-F ablation using catheters or hand-held probes. The mechanism for assessing transmurality may also be of value in the context of other types of ablation systems, including those in which ablation occurs in conjunction with an induced rise in tissue temperature, such as those applying ablation energy in the form of microwave radiation, light (laser ablation) or heat (thermal ablation). The invention may also be useful in conjunction with other types of ablation, including cryo-ablation, ultrasound ablation and chemical ablation.

According to the present invention, assessment of transmurality of a lesion is accomplished by monitoring the depolarization signal amplitude in a local electrogram taken using electrodes located adjacent the tissue to be ablated. In the context of R-F ablation, measurement of electrogram amplitude may be done using the ablation electrodes or may be done using dedicated electrodes adjacent to the ablation electrodes. In the context of the other types of ablation discussed above, electrogram measurement would typically be accomplished by means of a dedicated set of measurement electrodes.

Following onset of application of ablation energy to heart tissue, the amplitude of a local electrogram measured with electrodes located adjacent tissue to be ablated first gradually drops and then stabilizes, indicating that the tissue being monitored has ceased making any contribution to the sensed electrogram. The amplitude drop (ΔEGM) or the following amplitude plateau "P" may be used alone or together as indicators of transmurality employed by the present invention. The amplitude drop may be compared to a pre-set value (ΔEGM ? a). (The plateau "P" may be detected in response to a determination that the rate of amplitude change is less than a defined value over a series of amplitude measurements or over a defined duration (|dA/dt|=b). In some embodiments, detection of a rapid drop in amplitude (dA/dt=d) may be employed as an indicator that the ablation process is proceeding too quickly and may be employed to trigger a reduction in the power of applied ablation energy. In other embodiments, detection of an insufficiently rapid drop in amplitude (dA/dt=d) may be employed as an indicator that the ablation process is proceeding too slowly and may be employed to trigger an increase in the power of applied ablation energy.

In the context of R-F ablation, the invention is believed valuable in conjunction with an ablation device having multiple, individually activatable electrodes or electrode pairs to be arranged along a desired line of lesion. In this context, the mechanism for determining transmurality of lesions adjacent individual electrodes or pairs may be used to deactivate individual electrodes or electrode pairs, when the lesions in tissue adjacent these individual electrodes or electrode pairs are complete. This allows the creation of an essentially uniform lesion along the line of electrodes or electrode pairs, regardless of differences in tissue thickness adjacent the individual electrodes or electrode pairs. The invention is also believed useful in conjunction with assessment of transmurality of lesions produced by devices having only a single electrode or single electrode pair. Similar considerations apply to the use of the present invention in the contexts of other types of ablation as listed above.

DETAILED DESCRIPTION PREFERRED EMBODIMENTS

Figure 1:
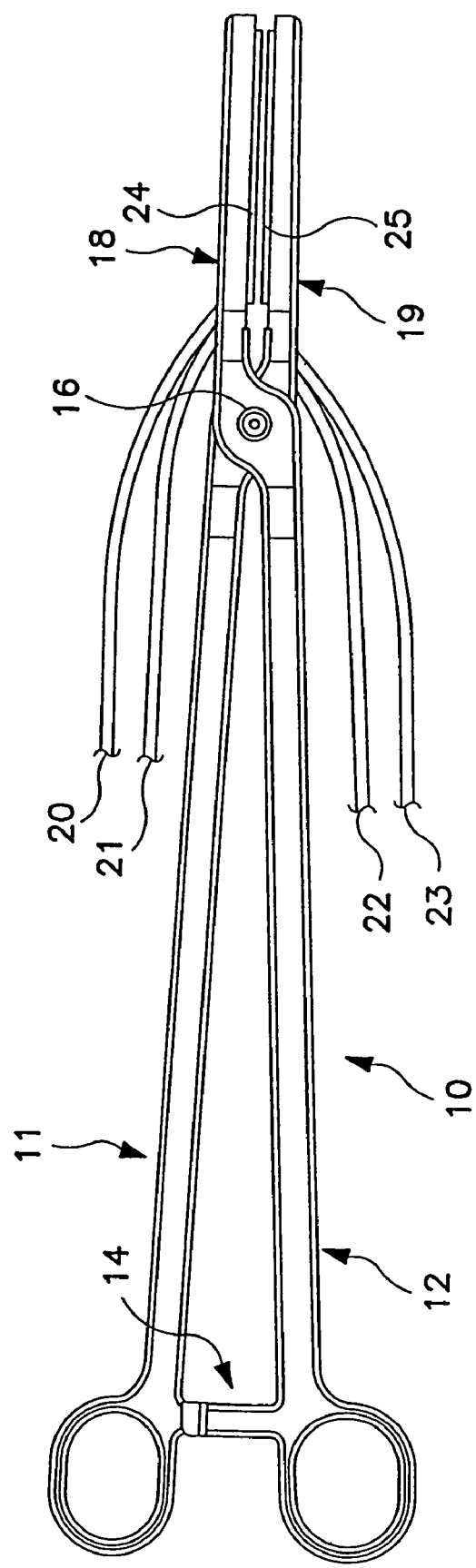
FIG. 1 is a plan view of a type of electrosurgical hemostat that may be used in conjunction with the present invention.

FIG. 1 is a plan view of a bipolar, saline irrigated electrosurgical hemostat of a type that may be employed in conjunction with the present invention. The hemostat is provided with elongated handles 11 and 12 and a lock mechanism 14, similar to a conventional surgical hemostat. The handles are connected to one another by pivot or hinge 16, and continue distally in the form of elongated jaws 18 and 19. Jaws 18 and 19 carry an elongated electrode or series of electrodes 24, 25, respectively, to which ablation energy, e.g. RF energy is applied by means of conductors 21 and 22. The electrodes are adapted to be irrigated by a saline solution or other conductive fluid along their length, provided via inlet tubes 20 and 23. In operation, tissue to be ablated is compressed between the jaws, and RF energy is applied between the electrode or electrode sets 24 and 25, as generally described in U.S. Pat. No. 6,096,037 issued to Mulier et al incorporated herein by reference in its entirety.

Figure 2A:
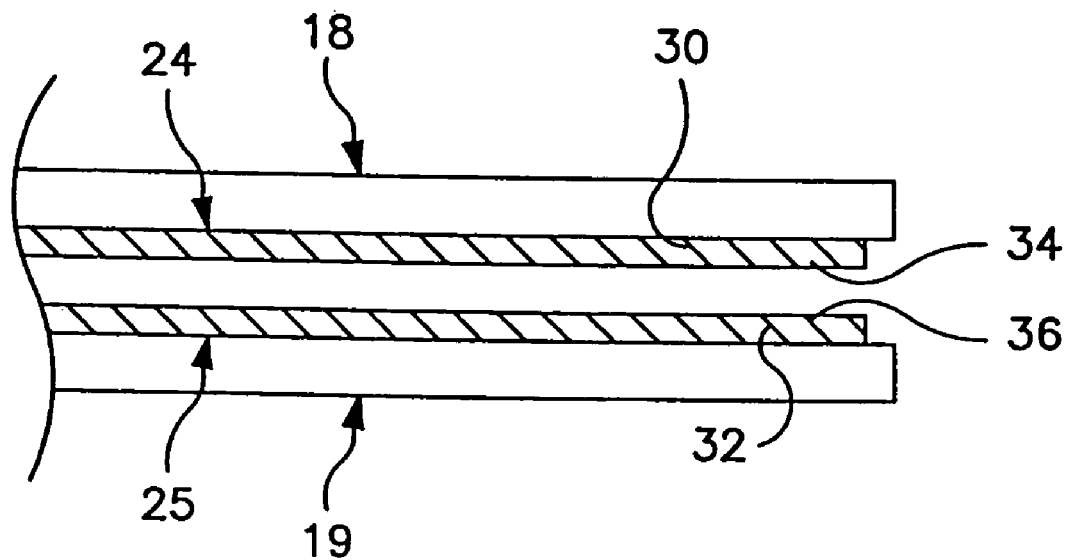
FIGS. 2a and 2b illustrate alternative electrode configurations for a hemostat generally according to FIG. 1.

FIG. 2a shows a first embodiment of an electrode arrangement for a hemostat generally as illustrated in FIG. 1. Illustrated components correspond to identically numbered components in FIG. 1. In this embodiment, electrodes 24 and 25 take the form of elongated coil electrodes 30 and 32, mounted around porous tubes 34 and 36, through which saline or other conductive fluid is delivered. The arrangement of the electrodes may also be reversed, for example placing coils 30 and 32 within elongated porous tubes 34 and 36, to accomplish a similar result. Alternatively, any other arrangement for providing an elongated electrode and delivery of saline solution along the length thereof may be substituted. The particular configuration of the electrode is not critical to the present invention. For example, irrigated electrodes corresponding to those described in U.S. Pat. No. 6,096,037 issued to Mulier, et al., U.S. Pat. No. 5,876,398 issued to Mulier, et al., U.S. Pat. No. 6,017,378 issued to Brucker, et al or U.S. Pat. No. 5,913,856 issued to Chia, et al., all incorporated herein by reference in their entireties may also be substituted. It should also be noted that while the electrode system as illustrated in FIG. 2a is a bipolar system, the invention may also be employed in conjunction with unipolar electrodes and/or in the form of a probe or a catheter. In some embodiments, irrigation of the electrodes may be omitted.

Figure 2B:
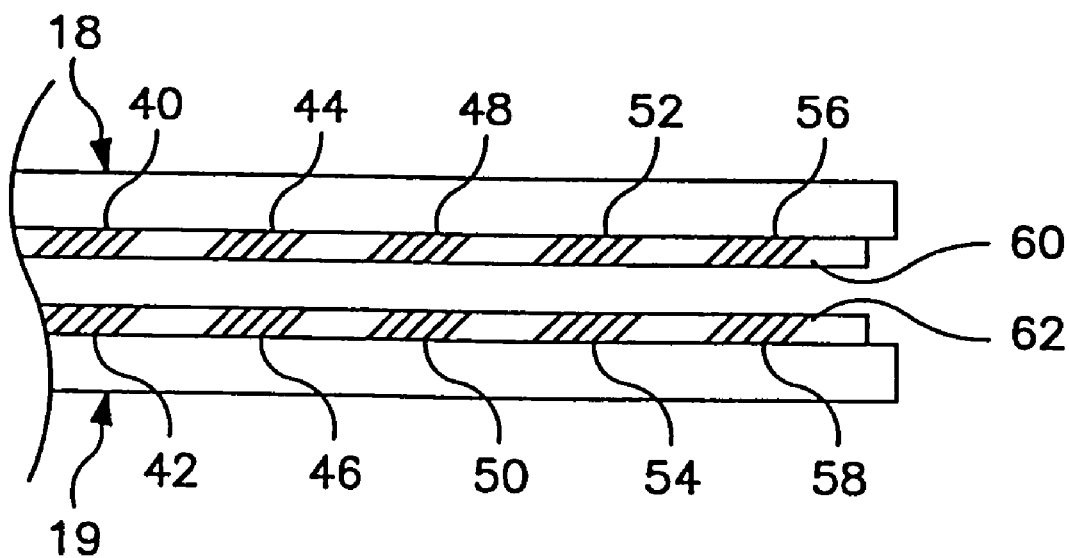

FIG. 2b illustrates an alternative embodiment of an electrode system for a hemostat generally as illustrated in FIG. 1. In this case, rather than a single pair of electrodes, multiple electrode pairs are provided. The electrode pairs comprise coil electrodes 40 and 42, 44 and 46, 48 and 50, 52 and 54, and 56 and 58. However, other pairings of electrodes might also be substituted, for example, pairing electrodes 40 and 44, electrodes 48 and 52 or the like. In this embodiment, the electrode pairs are mounted around porous plastic tubes 60 and 62 through which saline or other electrically conductive fluid is delivered. As in the case with the embodiment of FIG. 2a, the arrangement of these electrodes may readily be reversed, placing the electrodes within the lumen of plastic tube 60 or 62 and any other arrangement providing multiple, irrigated electrodes may also be substituted. As in the case of the embodiment of FIG. 2a, unipolar electrodes might be substituted for the multiple bipolar pairs as illustrated and/or the invention may be practiced in conjunction with a multi-electrode probe or catheter.

In use, the hemostat is arranged so that the tissue to be ablated is located between the jaws 18 and 19, and pressure is applied in order to compress the tissue slightly between the jaws to ensure good electrical contact. All electrode pairs may be activated individually and may be individually deactivated when the lesions between the individual electrode pairs are completely transmural. Alternatively, electrode pairs could be activated sequentially, with one pair deactivated upon a detection of a complete lesion between the electrode pair, followed by activation of the next sequential electrode pair. Corresponding use of the invention in conjunction with a series of unipolar electrodes, for example corresponding to electrodes along one of the two jaws in conjunction with a remote ground plate or a similar series of individually activatable electrodes on a catheter or probe in conjunction with a ground plate is also possible.

Figure 3:
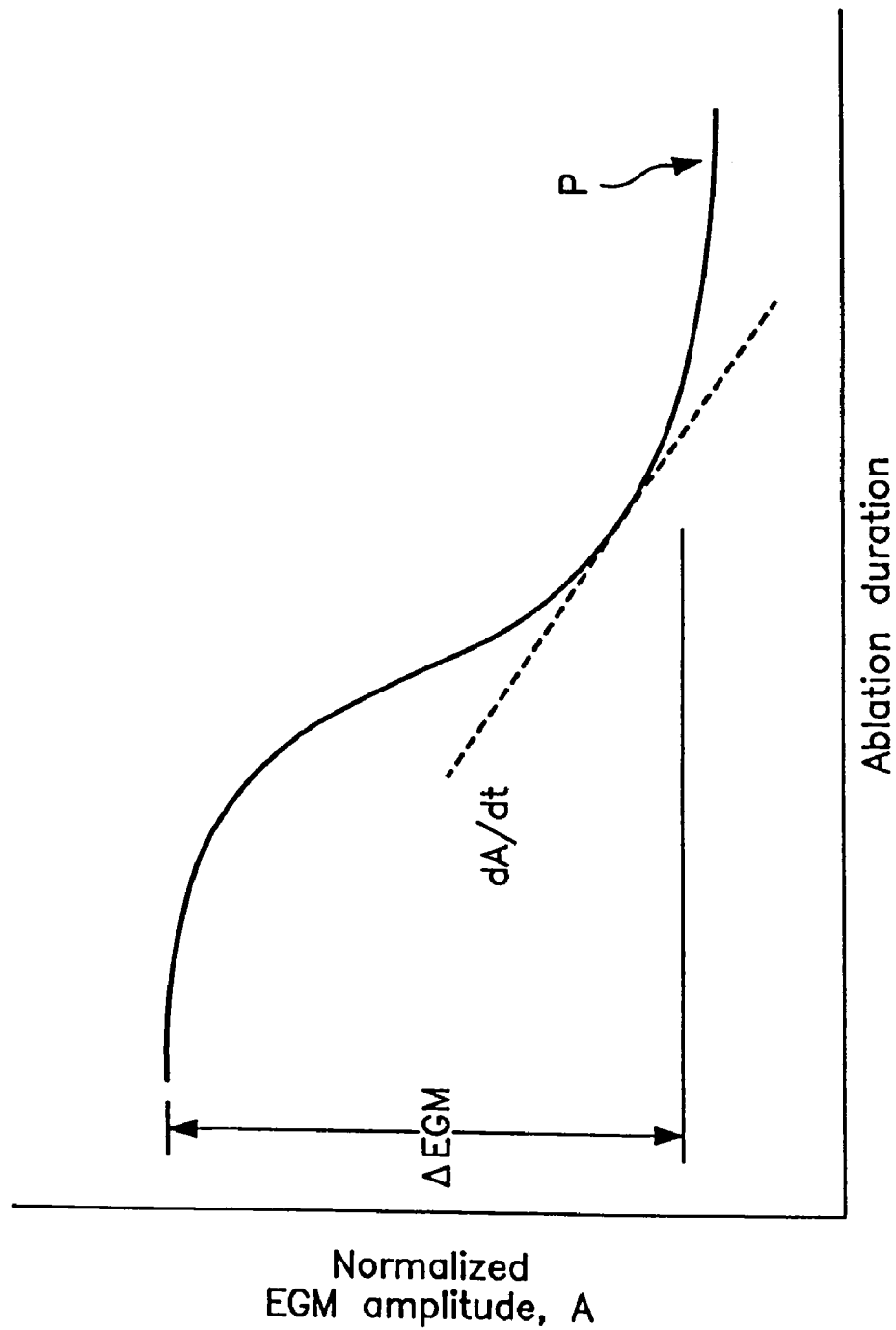
FIG. 3 illustrates the fall and plateau of electrogram amplitude measured using electrodes adjacent tissue during ablation.

FIG. 3 is a graph illustrating measured local electrogram amplitude "A" vs. time across tissue located between the electrodes of an irrigated bipolar hemostat as illustrated in FIG. 1. FIG. 3 illustrates the drop in electrogram amplitude followed by an amplitude plateau. The amplitude drop (ΔEGM) or the following amplitude plateau "P" may be used alone or together as indicators of transmurality employed by the present invention. In some embodiments, detection of a rapid rate of drop in amplitude (dA/dT) may be employed as an indicator that the ablation process is proceeding too quickly and may be employed to trigger a reduction in the power of applied ablation energy. In other embodiments, detection of an insufficient rate of drop in amplitude (dA/dT) may be employed as an indicator that the ablation process is proceeding too slowly and may be employed to trigger an increase in the power of applied ablation energy.

Figure 4:
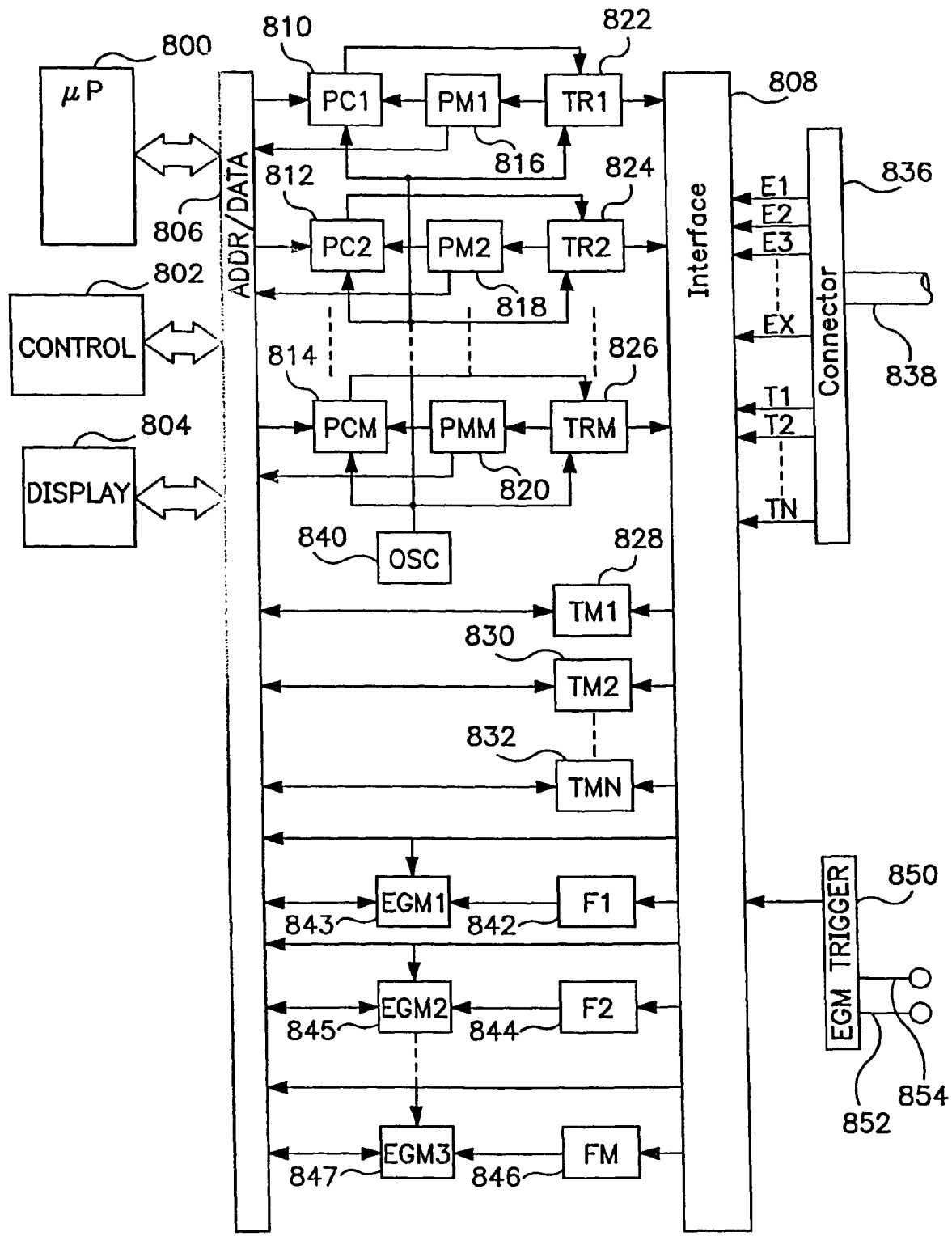
FIG. 4 is a functional block diagram of an RF generator appropriate for use in practicing the present invention, particularly adapted for use in conjunction with an ablation system employing multiple, individually activatable electrodes or electrode pairs.

FIG. 4 is a functional block diagram illustrating one embodiment of an R-F generator system for use in conjunction with the present invention. In this embodiment, separately controllable R-F outputs are provided for individual ablation electrodes or electrode pairs on an associated R-F ablation device, for example as in FIG. 2B. The R-F generator could of course also be used with ablation devices having only a single electrode or electrode pair as in FIG. 2A. With the exception of the electrogram amplitude measurement circuits discussed below, the generator corresponds generally to that described in conjunction with FIG. 16 of the '961 patent issued to Maguire, et al., cited above. The RF generator disclosed in the '961 patent provides feedback control of R-F power based upon either measured power (constant power) or measured temperature. The present invention is somewhat easier to implement in conjunction with the constant power mode, but may also be adapted to a temperature-regulated mode or to other feedback power regulation mechanism.

Display 804 and controls 802 are connected to a digital microprocessor 800, which permits interface between the user and the remainder of the electrical components of the system. Microprocessor 800 operates under control of stored programming defining its operation including programming controlling its operation according to the present invention, as discussed in more detail below. Microprocessor 800 provides control outputs to and receives input signals from the remaining circuitry via address/data bus 806. In particular, the microprocessor 800 provides for monitoring of power, current, voltage, electrogram amplitude and temperature. As necessary, the microprocessor will provide this information to the display 804. Additionally, the microprocessor 800 permits the user to select the control mode (either temperature or power) and to input the power set point, temperature set point, and a timer set point to the system. The primary source of power for the radio-frequency generator may be a 12 V battery rated at 7.2 ampere-hours or the device may be AC powered. A back-up battery (not shown) such as a lithium cell may also be provided to provide sufficient power to the microprocessor 800 to maintain desired memory functions when the main power is shut off.

The power supply system as illustrated includes a desired number "M" of individually controllable R-F power supplies and receives temperature inputs from a desired number "N" of temperature sensing devices in the ablation device, illustrated schematically at 838 and receives electrogram amplitude inputs from a desired number "M" of electrogram monitoring circuits. Each R-F power supply includes a transformer (822, 824, 826), a power control circuit (810, 812, 814) and a power measurement circuit (816, 818, 820). A crystal-locked radio-frequency oscillator 840 generates the switching pulses, which drive both the power transformers (822, 824, 826) and the power controllers (810, 812, 814). Power controllers (810, 812, 814) may be analog controllers which operate by pulse-width modulation by comparing a power set point signal from microprocessor 800 with an actual power signal generated by a power measurement circuit (816, 818, 820), which may, for example, include a.torroidal transformer coupled to the power output from the associated transformer (822, 824, 826). The power measurement circuits (816, 818, 820) multiply the output current and voltage and provide the resulting actual power signal to both the power controllers (810, 812, 814) and the microprocessor 800.

The R F power output of the transformers (822, 824, 826) is provided to interface board 808, and thereby is provided to the ablation electrode or electrodes on the ablation device 838. Separate analog comparator circuits (not illustrated) may also be provided for monitoring the output of the power measurement circuits (816, 818, 820), in order to shut-off current to the output transformers (822, 824, 826) if the power exceeds a limit, typically 55 watts. Power transformers (822, 824, 826) may include center taps, which receive the outputs of the power controllers (810, 812, 814). Secondary windings of the transformers (822, 824, 826) may provide for continuous monitoring of the applied voltage in order to permit the power calculations by power measurement circuits (816, 818, 820).

The illustrated power R-F generator system employs software controlled temperature processing, accomplished by micro processor 800, which receives the "N" temperature input signals from temperature measurement circuits (828, 830, 832), each of which are coupled to a corresponding temperature sensor in ablation device 838 by means of an electrical connector, illustrated schematically at 836 and interface circuit 808. If programmed to operate in the temperature controlled mode, processor 800 receives the "N" temperature signals and, based upon the indicated temperatures, defines power set points for each of the power control. circuits (810, 812, 814), which in the manner described above control the power levels applied to electrodes on the catheter through interface 834. Processor 800 may also selectively enable or disable any of the "M" provided R-F power supplies, in response to external control signals from controls 802 or in response to detected anomalous temperature conditions.

In addition to the circuitry as described above and disclosed in the Maguire, et al. '961patent, the apparatus of FIG. 4 includes multiple electrogram monitoring circuits EGM1, EGM2 . . . EGMM (843, 845 and 847 respectively), which may include one or more peak detectors coupled to sample and hold circuits, operating generally as described in U.S. Pat. No. 6, 266,566 issued to Nichols, et al., U.S. Pat. No. 6,029, 986 issued to Kim, et al., U.S. Pat. No. 6,095,150 issued to Panescue, et al. or U.S. Pat. No. 5,685,315, issued to McClure, et al., also all incorporated herein by reference in their entireties. The electrogram monitoring circuits measure electrogram amplitudes sensed using electrodes on the RF ablation device. Measured amplitudes may be peak-to-peak measurements of depolarization wave amplitudes or absolute peak value measurements, positive peak vales or negative peak values. Amplitude measurements employed in practicing the invention may be individually measured values or digitally filtered values obtained by averaging a series of individually measured amplitudes. The electrogram signals from the electrodes on the ablation device 838 may first be filtered through low-pass filters F1, F2, ... FN (842, 844, 846) and may be measured between the ablation electrodes or between electrodes located adjacent the ablation electrodes. Measurements are preferably made during interruptions in the delivery of ablation energy to the ablation electrodes, to minimize noise-sensing problems. Optionally, an EGM trigger circuit 850, coupled to surface EGM electrodes 852 and 854, may trigger electrogram measurement.

Individual electrogram amplitude measurements made by measurement circuits 843, 845 and 847 are provided to the address/data bus 806 and thence to microprocessor 800 for analysis to determine whether the behavior of the measured electrogram amplitude over time, indicates that the lesion associated with the measured amplitudes is completely transmural. As discussed in more detail below, a determination of transmurality may be made in response to detection of a defined drop in electrogram amplitude and/or a series of amplitude measurements that are relatively constant, over a desired period of time or over a defined number of successive amplitude measurements. In some embodiments, an abrupt drop in electrogram amplitude may also be employed to reduce the power level of ablation energy delivered to the tissue being monitored.

In cases in which an alternative ablation energy generation apparatus is employed, particularly those in which a rise in tissue temperature is induced, e.g. laser, microwave or thermal ablation, the R-F generation circuitry of FIG. 4 would be replaced with a corresponding alternative ablation energy generation apparatus. The measurement of electrogram amplitude and its use according to the present invention, however, may still be useful in conjunction with these alternative ablation energy generation systems. Similarly, he measurement of electrogram amplitude and its use according to the present invention may also be useful in conjunction with other forms of ablation such as cryo-ablation, ultrasound ablation and chemical ablation.

Figure 5:
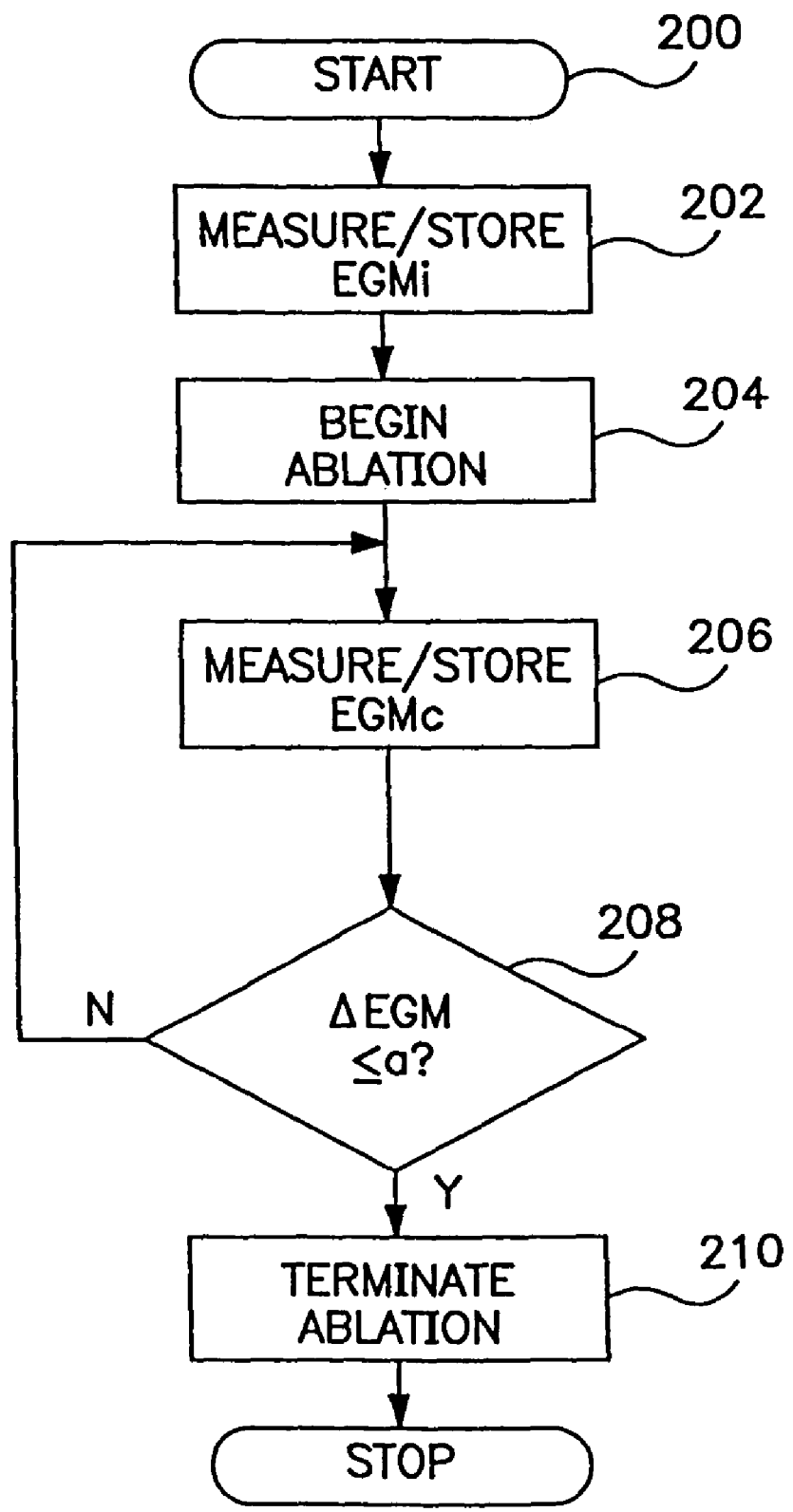
FIG. 5 is a functional flow chart illustrating a first mode of operation of the device illustrated in FIG. 4 in practicing the present invention.

FIG. 5 is a functional flow chart illustrating the operation of a device as in FIG. 4, according to the present invention. The flow chart of FIG. 5 illustrates operation of the device of FIG. 4 to control provision of R-F energy to an individual electrode or electrode pair. In the event that multiple electrodes or electrode pairs are employed, the control methodology of FIG. 5 would be applied to each electrode or electrode pair individually, as discussed in more detail below in conjunction with FIGS. 10 and 11.

The flow chart of FIG. 5 illustrates a method of assessing transmurality and terminating delivery of ablation energy to an electrode or an electrode pair responsive to detection of a specified drop in electrogram amplitude, e.g. a 75% drop. Following the detection of required amplitude drop, the device may wait a defined time period to assure completion of the lesion and then terminate the application of ablation energy to the associated electrode pair. Alternatively, termination of application of ablation energy may occur concurrent with detection of the required amplitude drop. Measurement of electrogram amplitude in tissue adjacent with the ablation electrode or electrode pair electrode pair may be made using the ablation electrodes themselves or using electrodes located in proximity to the ablation electrodes, for example corresponding to those used to measure impedance in the described in Yates '671 patent, incorporated by reference above.

After initialization at 200, the microprocessor 800 (FIG. 4) causes the electrogram measurement circuitry associated with the electrode or electrode pair being evaluated to acquire a base line or initial amplitude value $EGM_i$ at 202. The microprocessor then begins application of ablation energy to the monitored tissue at 204. During application of ablation energy, at defined intervals or in response to trigger signals from an EGM trigger circuit (850, FIG. 4) the microprocessor obtains and stores electrogram measurements at 206. Delivery of ablation energy may be interrupted during the electrogram measurement period. With each obtained amplitude measurement, the processor determines whether the required amplitude drop has occurred. This determination may be made, for example, in response to the first amplitude measurement below a preset required drop value "a", e.g. −75%, to a series of a required number of measured amplitudes below the required drop value, e.g. 2 or 3 measurements, or to a required proportion of measured amplitudes below the required drop value, e.g. 2 of 3 measurements. Alternatively, as noted above, averaged amplitudes may be calculated with each measurement, in which case a drop in the averaged amplitude may be employed to detect transmurality. Ablation and electrogram measurement continues until the required drop has been detected at 208. The termination of application of ablation energy to the tissue being monitored then occurs at 210. The termination of ablation may occur concurrent with detection of the required drop or a preset delay thereafter to assure complete transmurality.

Figure 6:
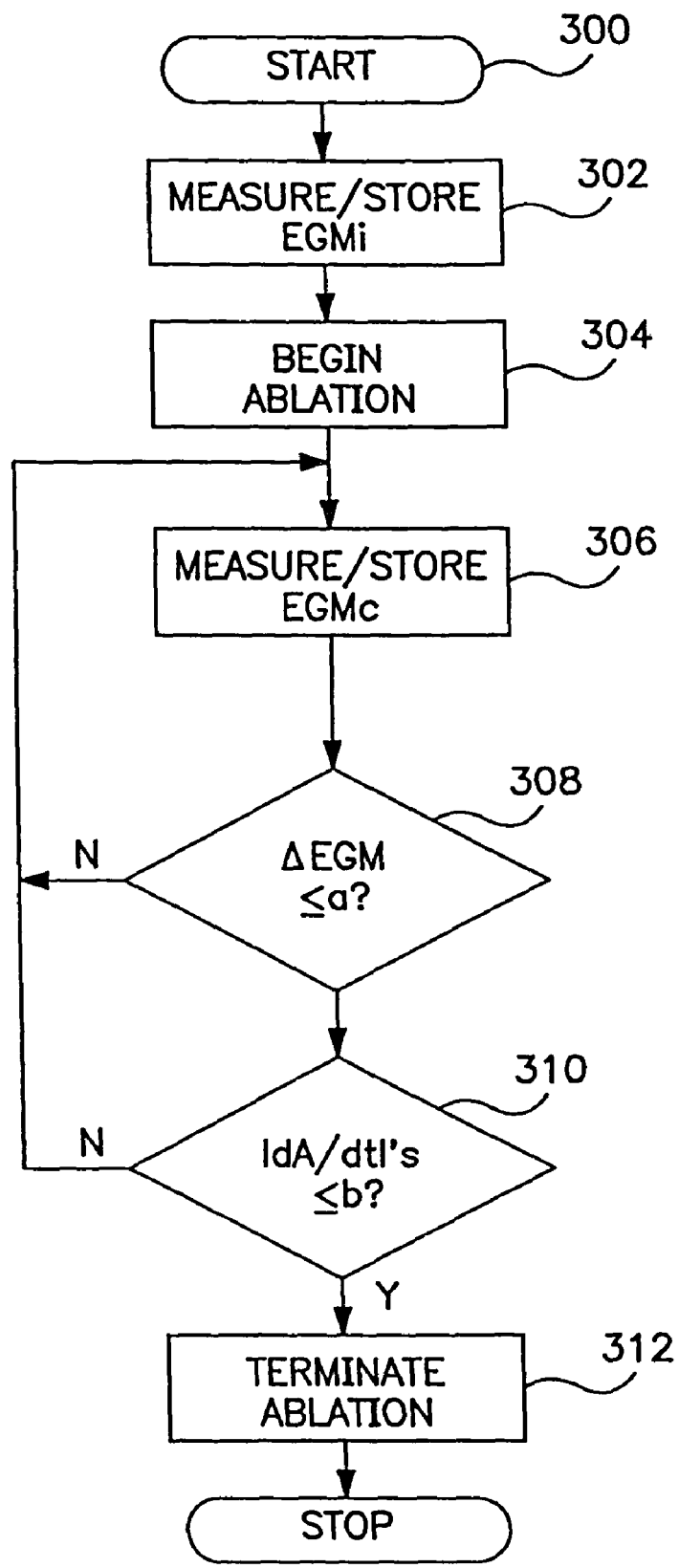
FIG. 6 is a functional flow chart illustrating a first alternative mode of operation of a device as in FIG. 4 in practicing the present invention.

FIG. 6 is a functional flow chart illustrating the operation of a device as in FIG. 4, according to a second embodiment of the present invention. The flow chart of FIG. 6 illustrates operation of the device of FIG. 4 to control provision of R-F energy to an individual electrode or electrode pair. In the event that multiple electrodes or electrode pairs are employed, the control methodology of FIG. 6 would be applied to each electrode or electrode pair individually, as discussed in more detail below in conjunction with FIGS. 10 and 11.

The flow chart of FIG. 6 illustrates a method of assessing transmurality and terminating delivery of ablation energy to an electrode or an electrode pair responsive to detection of a specified drop in electrogram amplitude, e.g. a 75% drop in conjunction with detection of an electrogram amplitude plateau. Following the detection of the required amplitude drop and plateau, the device may wait a defined time period to assure completion of the lesion and then terminate the application of ablation energy to the associated electrode pair. Alternatively, termination of application of ablation energy may occur concurrent with detection of the required amplitude drop and plateau. Measurement of electrogram amplitude in tissue adjacent with the ablation electrode or electrode pair electrode pair may be made using the ablation electrodes themselves or using electrodes located in proximity to the ablation electrodes.

After initialization at 300, the microprocessor 800 (FIG. 4) causes the electrogram measurement circuitry associated with the electrode or electrode pair being evaluated to acquire a baseline or initial amplitude value $EGM_i$ at 302. The microprocessor then begins application of ablation energy to the monitored tissue at 304. During application of ablation energy, the microprocessor obtains and stores electrogram measurements at 306, as discussed above in conjunction with FIG. 5. With each obtained amplitude measurement, the processor determines whether the required amplitude drop has occurred at 308. This determination may be made as described above in conjunction with FIG. 5.

If the required drop is detected at 308, at 310, the microprocessor 800 employs the stored electrogram amplitude measurements to calculate dA/dt, which may, for example, be calculated based on net variation of electrogram amplitude over a series of 2 or 3 measurements. As discussed above in conjunction with detection of the required amplitude drop, averaged amplitude values may also be used to calculate dA/dt. The absolute value of dA/dt, i.e., |dA/dt| may employed to assess whether or not an electrogram amplitude plateau has been reached at 310, for example by verifying that a series of values of |dA/dt| are all (e.g. 3 of 3) or predominantly (e.g. 2 of 3) below a defined variability value "b".

The processor continues to collect amplitude measurements and make calculations until such time as an amplitude plateau is recognized at 310 and a sufficient amplitude drop is recognized at 308. When both of these criteria have been met, the termination of application of ablation energy to the tissue being monitored then occurs at 312. The termination of ablation may occur concurrent with detection of the required drop or a preset delay thereafter to assure complete transmurality.

Figure 7:
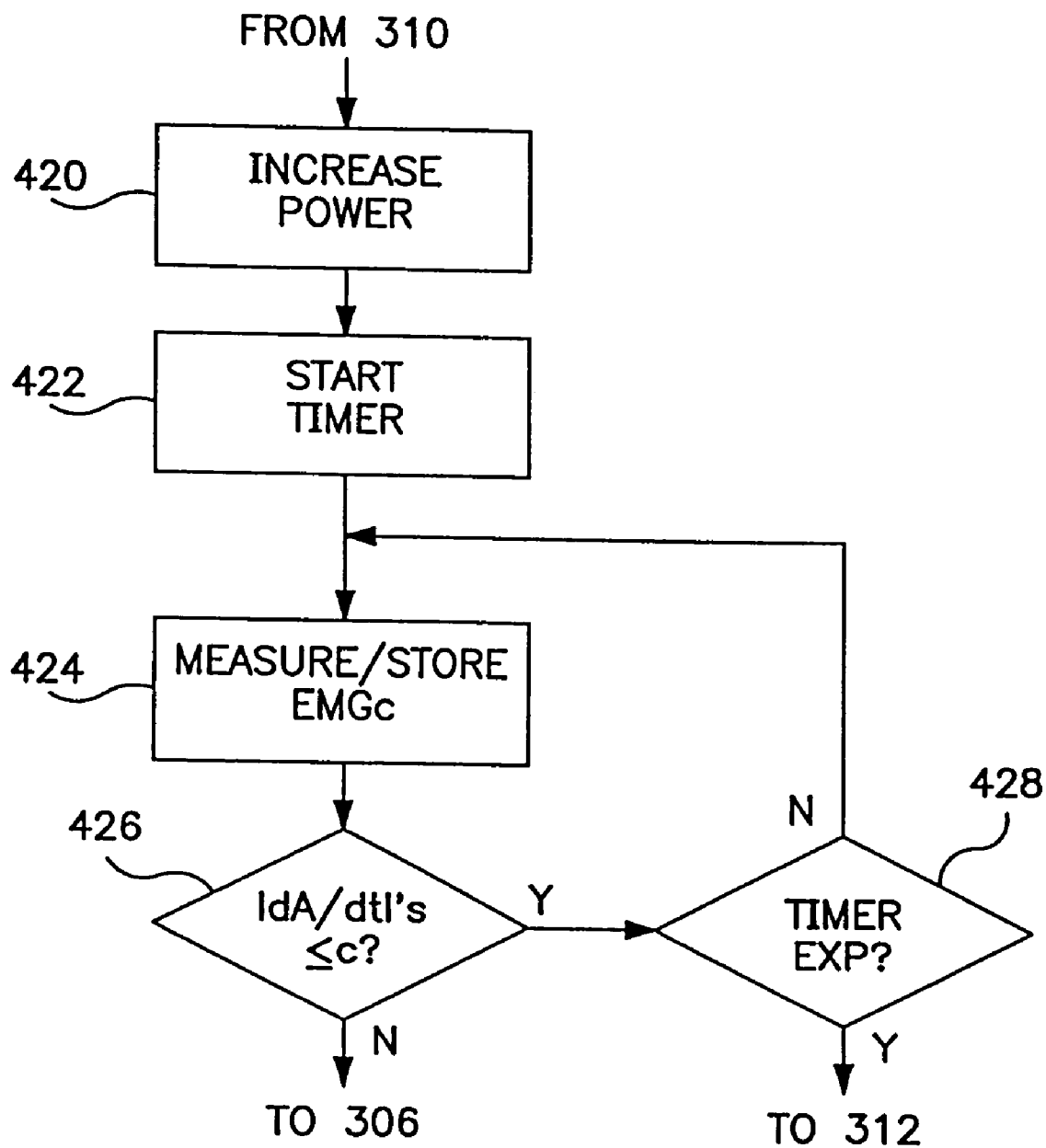
FIG. 7 is a functional flow chart illustrating a modification to the mode of operation according to FIG. 6.

FIG. 7 is a functional flow chart illustrating an optional additional set of operations for implementing a transmurality measurement method generally as in FIG. 6. The additional operations provide for an increase in ablation energy responsive to detection of an electrogram amplitude plateau at 310 (FIG. 6), in order to verify that ablation is complete. The processor triggers an increase in power at 420, for example 5 to 25%, and starts time period of a few seconds at 422. Measurement and calculation of electrogram amplitudes continues at 424 until either a significant drop in amplitude is detected at 426 or the timer expires at 428. If a significant drop is detected, for example the same magnitude of drop that would have prevented plateau detection at 310 (FIG. 6), the processor re-initiates the process of detecting a plateau at 306 (FIG. 6). If the time period expires with no further significant drop in electrogram amplitude, the processor terminates the ablation process at 312 (FIG. 6).

Figure 8:
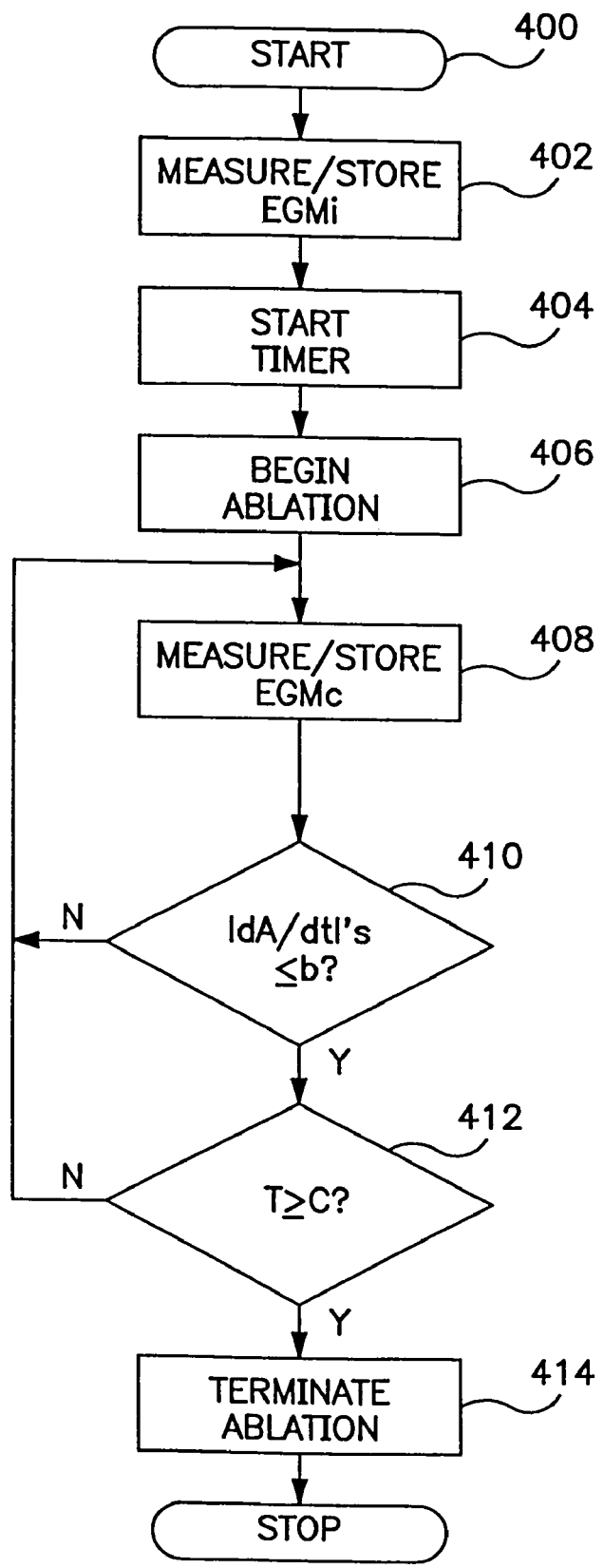
FIG. 8 is a functional flow chart illustrating a second alternative mode of operation of a device as in FIG. 4 in practicing the present invention.

FIG. 8 is a functional flow chart illustrating the operation of a device as in FIG. 4, according to an additional alternative embodiment of the present invention. The flow chart of FIG. 8 illustrates operation of the device of FIG. 4 to control provision of R-F energy to an individual electrode or electrode pair. In the event that multiple electrodes or electrode pairs are employed, the control methodology of FIG. 8 would be applied to each electrode or electrode pair individually, as discussed in more detail below in conjunction with FIGS. 10 and 11.

The flow chart of FIG. 8 illustrates a method of assessing transmurality and terminating delivery of ablation energy to an electrode or an electrode pair responsive to detection of an electrogram amplitude plateau in conjunction with a defined minimum ablation duration. Following the detection of the required plateau, the device may wait a defined time period to assure completion of the lesion and then terminate the application of ablation energy to the associated electrode pair. Alternatively, termination of application of ablation energy may occur concurrent with detection of the required amplitude drop and plateau. Measurement of electrogram amplitude in tissue adjacent with the ablation electrode or electrode pair electrode pair may be made using the ablation electrodes themselves or using electrodes located in proximity to the ablation electrodes.

After initialization at 400, the microprocessor 800 (FIG. 4) causes the electrogram measurement circuitry associated with the electrode or electrode pair being evaluated to acquire a base line or initial amplitude value $EGM_i$ at 402. The microprocessor then starts a duration time interval at 404 and begins application of ablation energy to the monitored tissue at 406. During application of ablation energy, the microprocessor obtains and stores electrogram measurements at 408, as discussed above in conjunction with FIG. 5. With each obtained amplitude measurement, the processor 800 determines whether an amplitude plateau has occurred at 410, in the manner discussed above in conjunction with FIG. 6. If a plateau is detected, the processor check to see if the required minimum ablation time, e.g. 10 seconds, has elapsed at 412.

The processor continues to collect amplitude measurements until such time as an amplitude plateau is recognized at 410 and a sufficient time has elapsed at 412. When both of these criteria have been met, the termination of application of ablation energy to the tissue being monitored then occurs at 414. The termination of ablation may occur concurrent with detection of the required drop or a preset delay thereafter to assure complete transmurality.

Figure 9A:
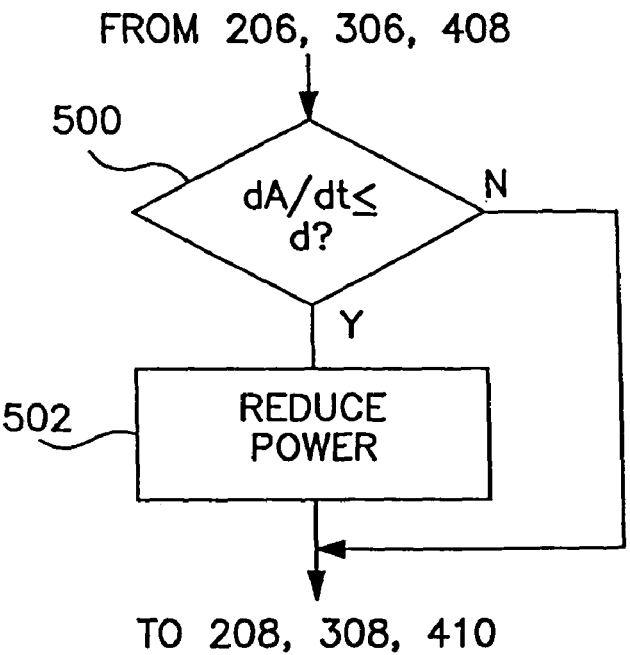
FIG. 9A is a functional flow chart illustrating a modification to the modes of operation according to FIGS. 5, 6 and 8.

FIG. 9A illustrates an additional set of operations for implementing a transmurality measurement method generally as in FIG. 5, 6 or 8. The operations of FIG. 8 may be performed following the measurement of electrogram amplitude at 206, 306 or 408 (FIGS. 5, 6 and 8). In the additional operations illustrated in FIG. 9A, the microprocessor checks at 500 to determine whether electrogram amplitude is decreasing too rapidly, for example in response to dA/dt having a value less than a defined negative threshold "d", e.g. −10 mv/s. In response to a detected excessive decrease at 500, the processor reduces the power level of the ablation energy being applied to the monitored tissue at 502 to slow the ablation process. Operation of the device then continues as in FIG. 5, 6 or 8.

Figure 9B:
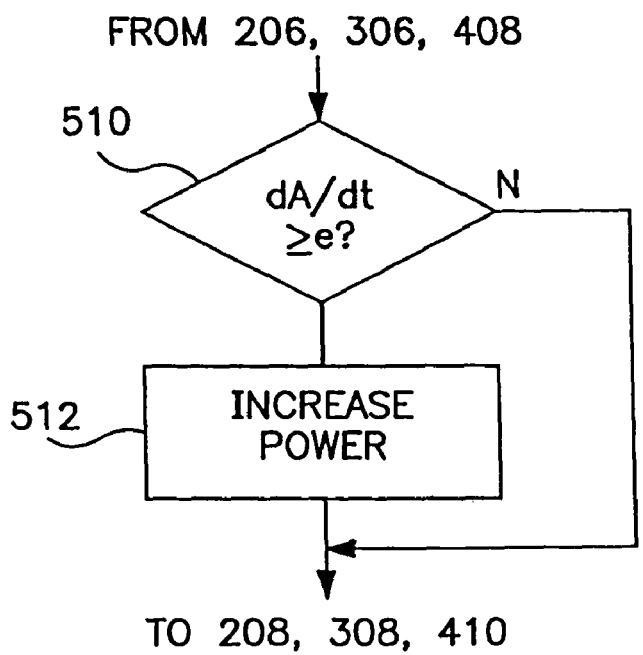
FIG. 9B is a functional flow chart illustrating an additional modification to the modes of operation according to FIGS. 5, 6 and 8.

FIG. 9B also illustrates an additional set of operations for implementing a transmurality measurement method generally as in FIG. 5, 6 or 8. The operations of FIG. 8 may be performed following the measurement of electrogram amplitude at 206, 306 or 408 (FIGS. 5, 6 and 8) and may be performed in conjunction with or instead of the operations of FIG. 9A. In the additional operations illustrated in FIG. 9B, the microprocessor checks at 510 to determine whether electrogram amplitude is decreasing too rapidly, for example in response to dA/dt having a value greater than a defined negative threshold "e", e.g. −1 mv/s. In response to a detected insufficient decrease at 510, the processor increases the power level of the ablation energy being applied to the monitored tissue at 512 to speed the ablation process. Operation of the device then continues as in FIG. 5, 6 or 8.

Figure 10:
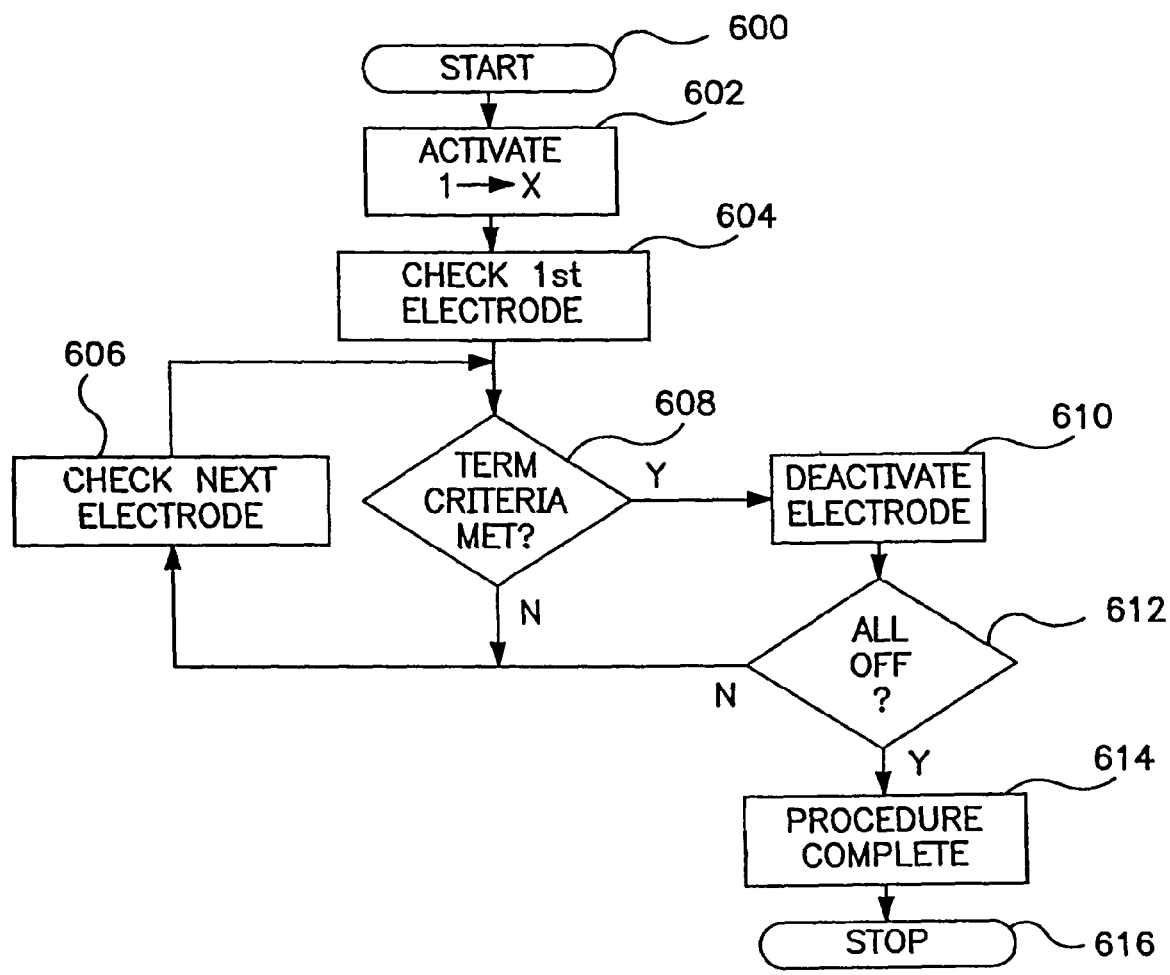
FIG. 10 is a functional flow chart illustrating a first method of operation of a device as in FIG. 4 to activate and deactivate individual electrodes or electrode pairs.

FIG. 10 is a functional flow chart illustrating the over-all operation of the device in conjunction with a multi electrode or multi electrode pair ablation apparatus. In the flow chart of FIG. 10, all the ablation electrodes or electrode pairs are activated simultaneously and individual ablation electrodes or electrode pairs are deactivated in response to electrogram amplitude measurements associated with the electrode pair indicating that the lesion formed between that electrode pair is completely transmural. In this circumstance, the ablation system works as follows.

After initialization at 600, all electrodes 1-X are activated at 602, meaning that ablation energy is provided to all electrodes and electrode pairs. The microprocessor measures the electrogram amplitude associated with a first electrode or electrode pair at 604 and then at 608 checks to see whether transmurality criteria are met for a first ablation electrode or electrode pair at 604, using the criteria discussed above in conjunction with any of FIGS. 5-8. If so, the ablation electrode or electrode pair is deactivated at 610 by ceasing the delivery of ablation energy to the electrode or electrode pair. If not, the microprocessor measures the electrogram amplitude associated with the next ablation electrode or electrode pair at 606 and checks transmurality criteria for the next electrode at 608. This process continues until all electrodes are deactivated at 612, after which the procedure is deemed complete at 614 and the ablation process is terminated at 616.

Figure 11:
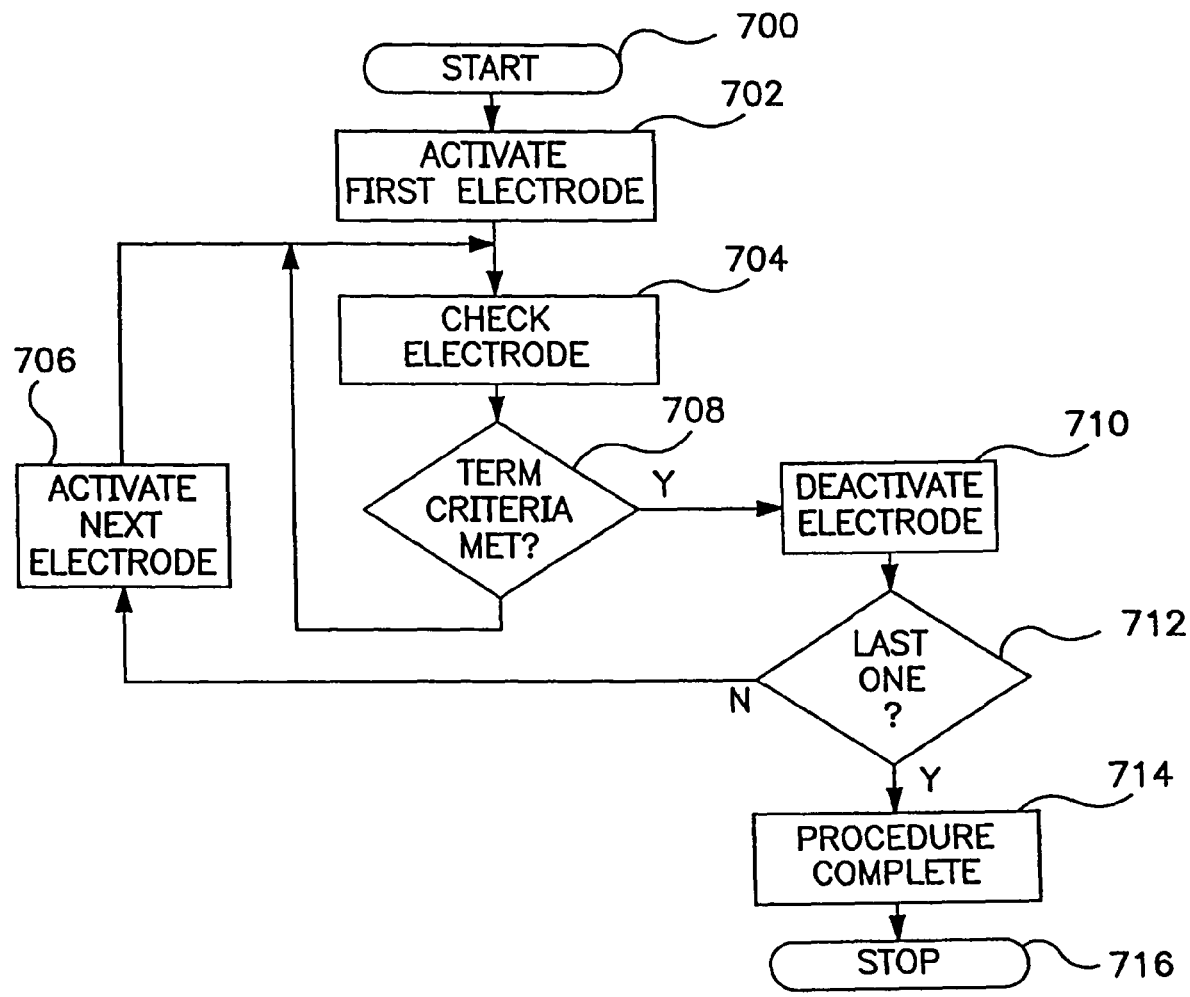
FIG. 11 is a functional flow chart illustrating a second method of operation of a device as in FIG. 4 to activate and deactivate individual electrodes or electrode pairs.

FIG. 11 illustrates a functional flow chart of overall operation of a device in which a multi-electrode or multi-electrode pair ablation apparatus is employed, as in FIG. 10. In this embodiment, however, ablation electrodes or electrode pairs are activated sequentially. After initialization at 700, the microprocessor activates delivery of ablation energy to the first ablation electrode or electrode pair at 702 and measures electrogram amplitude at 704. At 708, the processor and, in the same manner as described for FIG. 9 above, checks to determine whether transmurality criteria have been met. If so, the ablation electrode or electrode pair is deactivated at 710. If not, application of ablation energy continues until the transmurality criteria are met as described above. After deactivation of an electrode or electrode pair at 710, the microprocessor checks to determine whether all electrodes have been activated and deactivated at 712, if not, the microprocessor then activates the next electrode or electrode pair at 706 and initiates delivery of ablation energy to that electrode or electrode pair. This process continues until the last electrode has been deactivated at 712, following which the microprocessor determines that the ablation process is complete at 714 and the ablation process is stopped at 716.

The overall operational methodology of FIG. 10 is believed to be desirable in that it allows for a more rapid completion of an ablation procedure. However, the overall operational method is described in FIG. 11 has the advantage that it may allow the use of a somewhat simplified generator because that multiple, separate electrogram measurement circuits, power control circuits, and the like need not be provided for each electrode or electrode pair. A simple switching mechanism may be used in conjunction with only a single RF generator and electrogram measurement circuit to successively apply energy to each electrode and to monitor electrogram amplitude according to the invention.

In conjunction with the above specification, we claim:

1. An ablation system, comprising:
 a generator for generating ablation energy;
 an ablation device comprising an ablation element operably coupled to the generator and locatable adjacent a tissue site to be ablated, for applying ablation energy to the tissue site;
 an electrogram measurement element mounted to the ablation device so that the electrogram measurement element is adjacent the tissue site when the ablation element is adjacent the tissue site;
 electrogram amplitude measurement circuitry operably coupled to the electrogram measurement element to measure electrogram amplitude at the tissue site, using the electrogram measurement element; and
 control circuitry operably coupled to the generator to initiate and terminate the application of ablation energy to the ablation element, wherein the control circuitry is operably coupled to the electrogram amplitude measurement circuit and terminates application of ablation energy to the ablation element responsive to occurrence of a plateau in the electrogram amplitude measured by the electrogram amplitude measurement circuitry following initiation of application of ablation energy to the ablating element.

2. The system of claim 1 wherein the ablation element is an ablation electrode.

3. The system of claim 2 wherein the ablation electrode is an irrigated ablation electrode.

4. The system of claim 2 wherein the ablation electrode is employed as the electrogram measurement element.

5. The system of claim 1 wherein the electrogram measurement element is an electrogram measurement electrode.

6. The system of claim 1 wherein the generator is an R-F generator.

7. The system of claim 1 wherein the ablation energy is R-F energy.

8. The system of claim 1 wherein the ablation energy is microwave radiation.

9. The system of claim 1 wherein the ablation energy is laser energy.

10. The system of claim 1 wherein the ablation energy is heat energy.

11. The system of claim 1 wherein the ablation energy is ultrasound energy.

12. An ablation system, comprising:
 a generator for generating ablation energy;
 an ablation device comprising an ablation element operably coupled to the generator and locatable adjacent a tissue site to be ablated, for applying ablation energy to the tissue site;
 an electrogram measurement element mounted to the ablation device so that the electrogram measurement element is adjacent the tissue site when the ablation element is adjacent the tissue site;
 electrogram amplitude measurement circuitry operably coupled to the electrogram measurement element to measure electrogram amplitude at the tissue site, using the electrogram measurement element; and
 control circuitry operably coupled to the generator to initiate and terminate the application of ablation energy to the ablation element, wherein the control circuitry is operably coupled to the electrogram amplitude measurement circuit and reduces the level of ablation energy to the ablation element responsive to occurrence of a rapid drop in the electrogram amplitude measured by the electrogram amplitude measurement circuitry following initiation of application of ablation energy to the ablating element.

13. The system of claim 12 wherein the ablation element is an ablation electrode.

14. The system of claim 13 wherein the ablation electrode is an irrigated ablation electrode.

15. The system of claim 13 wherein the ablation electrode is employed as the electrogram measurement element.

16. The system of claim 12 wherein the electrogram measurement element is an electrogram measurement electrode.

17. The system of claim 12 wherein the generator is an R-F generator.

18. The system of claim 12 wherein the ablation energy is R-F energy.

19. The system of claim 12 wherein the ablation energy is microwave radiation.

20. The system of claim 12 wherein the ablation energy is laser energy.

21. The system of claim 12 wherein the ablation energy is heat energy.

22. The system of claim 12 wherein the ablation energy is ultrasound energy.

23. An ablation system, comprising:

a generator for generating ablation energy;

an ablation device comprising an ablation element operably coupled to the generator and locatable adjacent a tissue site to be ablated, for applying ablation energy to the tissue site;

an electrogram measurement element mounted to the ablation device so that the electrogram measurement element is adjacent the tissue site when the ablation element is adjacent the tissue site;

electrogram amplitude measurement circuitry operably coupled to the electrogram measurement element to measure electrogram amplitude at the tissue site, using the electrogram measurement element; and control circuitry operably coupled to the generator to initiate and terminate the application of ablation energy to the ablation element, wherein the control circuitry is operably coupled to the electrogram amplitude measurement circuit and terminates the application of ablation energy to the ablation element responsive to occurrence of a drop in the electrogram amplitude measured by the electrogram amplitude measurement circuitry following initiation of application of ablation energy to the ablating element.

24. The system of claim 23 wherein the ablation element is an ablation electrode.

25. The system of claim 24 wherein the ablation electrode is an irrigated ablation electrode.

26. The system of claim 24 wherein the ablation electrode is employed as the electrogram measurement element.

27. The system of claim 23 wherein the electrogram measurement element is an electrogram measurement electrode.

28. The system of claim 23 wherein the generator is an R-F generator.

29. The system of claim 23 wherein the ablation energy is R-F energy.

30. The system of claim 23 wherein the ablation energy is microwave radiation.

31. The system of claim 23 wherein the ablation energy is laser energy.

32. The system of claim 23 wherein the ablation energy is heat energy.

33. The system of claim 23 wherein the ablation energy is ultrasound energy.

* * * * *